US012440373B2

(12) United States Patent
Bayat et al.

(10) Patent No.: US 12,440,373 B2
(45) Date of Patent: Oct. 14, 2025

(54) DEVICE FOR CONTROLLED INJECTION ACROSS A VARIETY OF MATERIAL PROPERTIES

(71) Applicant: AESCULA TECH, INC., Los Angeles, CA (US)

(72) Inventors: Niki Bayat, Pasadena, CA (US); Adam Griese, Los Angeles, CA (US); Roby Menefee, Los Angeles, CA (US); Rahul Janardhanan, Los Angeles, CA (US); Jose Ramirez, Denver, CO (US)

(73) Assignee: AESCULATECH, INC., Los Angeles, CA (US)

( * ) Notice: Subject to any disclaimer, the term of this patent is extended or adjusted under 35 U.S.C. 154(b) by 0 days.

(21) Appl. No.: 18/009,897

(22) PCT Filed: Jun. 11, 2021

(86) PCT No.: PCT/US2021/036931
§ 371 (c)(1),
(2) Date: Dec. 12, 2022

(87) PCT Pub. No.: WO2021/252841
PCT Pub. Date: Dec. 16, 2021

(65) Prior Publication Data

US 2023/0233374 A1 Jul. 27, 2023

Related U.S. Application Data

(60) Provisional application No. 63/101,228, filed on Jun. 11, 2020.

(51) Int. Cl.
*A61F 9/00* (2006.01)
*A61F 9/007* (2006.01)
(Continued)

(52) U.S. Cl.
CPC ........ *A61F 9/0017* (2013.01); *A61F 9/00772* (2013.01); *A61L 31/048* (2013.01); *A61L 31/145* (2013.01)

(58) Field of Classification Search
CPC .... A61M 5/00; A61M 5/1452; A61M 5/1454; A61M 5/20; A61M 5/2033; A61M 5/2422; A61M 5/28; A61M 5/281
See application file for complete search history.

(56) References Cited

U.S. PATENT DOCUMENTS 2,660,168 A * 11/1953 Oswald .................. A61M 5/24 294/94
3,050,059 A * 8/1962 Wall .................. A61M 5/31513 604/222
(Continued)

FOREIGN PATENT DOCUMENTS

WO 20170158366 A2 9/2017
WO 2019008529 A1 1/2019
(Continued)

OTHER PUBLICATIONS

Rahco, "Natural Rubber", 2024 (Year: 2024).*
(Continued)

*Primary Examiner* — Kevin C Sirmons
*Assistant Examiner* — Antarius S Daniel
(74) *Attorney, Agent, or Firm* — Thomas | Horstemeyer, LLP

(57) ABSTRACT

Described herein is a generalized injection device for delivering formulations of various mechanical properties to precise locations. Of particular interest is the manifestation intended for the application of a thermally responsive hydrogel to the tear duct for the purpose of occlusion, as a treatment for symptoms associated with dry eye syndrome. Further, a modular solution to the need for an injection device across a variety of applications, mechanism, and
(Continued)

physical considerations is provided. This disclosure provides examples of methods for precise injection of low volumes, moisture retention in pre-filled injection devices, and actuation for automatic or manual injection, to name a few.

86 Claims, 16 Drawing Sheets

(51) Int. Cl.
*A61L 31/04* (2006.01)
*A61L 31/14* (2006.01)

(56) References Cited

U.S. PATENT DOCUMENTS

| | | | | |
|---|---|---|---|---|
| 3,055,362 | A * | 9/1962 | Uytenbogaar | A61M 5/2053 604/197 |
| 3,517,668 | A | 6/1970 | Brickson | |
| 8,439,865 | B2 | 5/2013 | Lust et al. | |
| 9,539,139 | B2 * | 1/2017 | Andino | A61J 1/201 |
| 10,463,572 | B2 * | 11/2019 | Shor | A61M 5/345 |
| 2005/0159707 | A1 | 7/2005 | Schiller | |
| 2006/0100591 | A1 | 5/2006 | Alhedit et al. | |
| 2009/0036868 | A1 | 2/2009 | Pinedjian et al. | |
| 2010/0292651 | A1 | 11/2010 | Yodfat et al. | |
| 2011/0224610 | A1 * | 9/2011 | Lum | A61M 5/3145 141/2 |
| 2013/0274666 | A1 * | 10/2013 | Brereton | A61M 5/46 604/117 |
| 2013/0303985 | A1 * | 11/2013 | Wotton | A61M 5/2033 604/218 |
| 2014/0228746 | A1 * | 8/2014 | Bartlett, II | A61J 1/2093 604/220 |
| 2015/0165129 | A1 * | 6/2015 | Row | A61M 5/31501 604/189 |
| 2016/0144131 | A1 * | 5/2016 | Schwirtz | A61M 5/3204 604/198 |
| 2016/0175515 | A1 * | 6/2016 | Mccullough | A61M 5/20 604/65 |
| 2016/0310417 | A1 * | 10/2016 | Prausnitz | A61K 39/3955 |
| 2017/0014431 | A1 * | 1/2017 | Yoshida | A61K 9/0019 |
| 2017/0095369 | A1 * | 4/2017 | Andino | A61M 37/0015 |
| 2017/0319784 | A1 * | 11/2017 | Marsh | A61M 5/31585 |
| 2018/0228482 | A1 | 8/2018 | Madsen et al. | |
| 2018/0303866 | A1 * | 10/2018 | Brown | A61K 47/24 |
| 2018/0344933 | A1 * | 12/2018 | Dittrich | A61M 5/286 |
| 2018/0360743 | A1 * | 12/2018 | Bartynski | A61P 27/02 |
| 2019/0142433 | A1 * | 5/2019 | Hopkinson | A61B 17/12109 606/194 |
| 2019/0216516 | A1 | 7/2019 | Vogt et al. | |
| 2019/0366000 | A1 * | 12/2019 | Cowe | A61M 5/2422 |
| 2020/0009323 | A1 * | 1/2020 | Nair | A61M 5/24 |
| 2020/0069889 | A1 | 3/2020 | Lin | |
| 2020/0093992 | A1 * | 3/2020 | Gibson | A61M 5/31513 |
| 2020/0215269 | A1 * | 7/2020 | Yotsutsuji | A61M 5/31515 |
| 2020/0268985 | A1 * | 8/2020 | Shaw | A61M 5/3221 |
| 2020/0330695 | A1 * | 10/2020 | Provonchee | A61J 1/2086 |
| 2021/0069426 | A1 * | 3/2021 | Huculak | A61M 5/281 |
| 2021/0228806 | A1 * | 7/2021 | Streeter | A61M 5/1782 |

FOREIGN PATENT DOCUMENTS

| | | |
|---|---|---|
| WO | 2019043784 A1 | 3/2019 |
| WO | 2019094702 A1 | 5/2019 |
| WO | 2019136238 A1 | 7/2019 |

OTHER PUBLICATIONS

U.S.NRC, "Doses in our daily lives", Apr. 26, 2022 (Year: 2022).*
Azo, "Silicone Rubber", Sep. 25, 2001, Azo Materials (Year: 2001).*
International Search Report for PCT/US21/36931 mailed Sep. 30, 2021.
Keller, et al., Pacific Northwest National Laboratory, Jan. 31, 2017. Water Vapor Permeation in Plastics.
Labthink, Among all the current standards for rubber materials, Abstract, Among all the current standards for rubber matters, and stamps; Dec. 31, 2016.
NR—natural rubber, Rahco Rubber, Jul. 12, 2017.
Office Action for China Pat. Application No. 202180039444.4 received Aug. 31, 2024.
International search report PCT/US2021/036931 mailed Jun. 11, 2024.
Search Report for TW Application No. 110121488 mailed Jan. 3, 2025.

* cited by examiner

| PART NUMBER | PART DESCRIPTION |
|---|---|
| 1 | Body comprises of one or more components that serve as the primary physical feature(s) allowing the user to grip and manipulate the device. The body may contain and protect other components and/or act as the reservoir for the fluid being injected. |
| 2 | Injection port is the feature that last contacts the injected fluid. Outer diameter of the port is driven by the dimensions of the target. The inner diameter of the port affects the fluid injection velocity. The wall thickness, material, and exposed length affect the mechanical resistance to deformation of the port. The injection port may be likened to a needle. |
| 3 | Reservoir is the location where the fluid is staged prior to injection. Prior to filling the reservoir, this comprises some empty space within an enclosing geometry. The geometry of the reservoir affects the fluid dynamics at the time of injection. |
| 4 | Pressurization Components comprises one or more components which undergo movement – either translational, rotational, or otherwise – that cause them to gradually reduce the volume of open space connected to the fluid reservoir. This is usually done with a seal having been created between the pressurization component(s) and the chamber/reservoir being encroached upon, but is not strictly necessary. By virtue of reducing the volume in the reservoir, there will be an increase in pressure, causing the contents of the reservoir to escape through any patent outlets. |
| 5 | Activation Trigger comprises one or more components which cause – or remove impediment to – the movement of the Actuation Mechanism(s). The Activation Trigger is the primary component of the user interface that allows the user to easily perform a particular function of the device, such as injection. Fundamentally, this may be said to occur when an external force is applied in a specific location and/or disposition. The trigger can either transmit force or simply result in movement. |
| 6 | Actuation Mechanism comprises one or more components which actuate the pressurization components. This actuation event may be incited by the activation trigger. Fundamentally, mechanism activation may be said to be the transmission of active or passive kinetic energy. This will result in movement of the pressurization component(s). Note that the activation trigger, actuation mechanism and pressurization components, may all be one and the same, as may be considered the case for a plunger pushed by thumb. |
| 7 | A cap is a common component for protecting device components, such as the injection port, and for limiting their exposure. Described in FIG. 1 is a cap that has been integrated with a tool commonly used by ophthalmologists – a dilator. A dilator is used to dilate the punctum of the tear duct. This component serves the dual purpose of a cap and of a dilator, where the body of the injection device also serves as the body of the dilator. |
| 8 | Securing components are a common aspect in many devices. Screws, adhesives, press-fits, among others may be used to ensure that components mate effectively and maintain their position under external force. |
| 9 | Hub is a component used to control the exposed length of the injection port and to provide a smooth contact surface to assist with control of the injection port. The hub may contain and/or protect other components or features, such as the fluid reservoir (pre-filled or otherwise) and pressurization component(s). |
| 10 | Injection port cover is a component(s) used to protect the injection port and to control leakage. By creating a sealed environment at the outlet of the injection port, any ambient escape of fluid will be limited. The cover may be integrated into the cap so that both components may be removed from the device at once. |

FIG. 2

DEVICE FOR CONTROLLED INJECTION ACROSS A VARIETY OF MATERIAL PROPERTIES

CROSS REFERENCE TO RELATED APPLICATIONS

This application is the 35 U.S.C. § 371 national stage application of PCT Application No. PCT/US2021/036931, filed Jun. 11, 2021, which claims priority to, and the benefit of, U.S. Provisional Application No. 63/101,228, filed Jun. 11, 2020, both of which are hereby incorporated by reference herein in their entireties.

BACKGROUND

Many types of injection devices exist; some for general use, and some for specific applications. Their mode of action is also a unique factor, often drawn from the intended use.

In a clinical setting, interaction between human factors and device mechanisms ultimately affect the experience of both the user and the patient. Additionally, the dynamics of injection, arising from specific geometries, material properties, and mechanical forces, may have significant bearing on the placement and overall efficacy of the injected material.

In some cases, the injection procedure is delicate and requires both precision and speed. Similarly, the material being injected may have properties that must be specifically catered to, or else their intended function may be subverted when the rate of a change in material properties or other effect outpaces the intended use life, speed of administration, or other desired parameter.

SUMMARY

Described herein are examples of device configurations and usage manifestations for a novel injector and methods of use. To distinguish an expansion of scope from devices which are strictly paired with pharmaceuticals, this device is otherwise generally referred to as a device or an applicator. The configurations and manifestations include various mechanical actuators and nuanced design features which are scale-modular and enable a user-friendly functionality which is most useful for, but not exclusive to, single-use and low-volume applications, especially in the application of smart materials.

In one aspect, among others, an injection device comprises an injection port configured to deliver a shape adaptable material; a junction component coupled to a body of the injection device and to the injection port, the junction component comprising a reservoir configured to contain the shape adaptable material for ejection through the injection port; and an actuation mechanism comprising a stopper that engages with and seals the reservoir, where activation of the actuation mechanism forces the stopper into the reservoir thereby controlling ejection of the shape adaptable material through the injection port. In one or more aspects of these embodiments, the actuation mechanism can comprise a spring that forces the stopper into the reservoir via a plunger. The spring can be a compression spring sized to provide an axial force based upon properties of the shape adaptable material being ejected. The spring can be extended when the actuation mechanism is activated. The spring can be compressed to a fully loaded length in a range from about 10% to about 50% of a free length of the spring before activation. Extension of the spring can impart a force to a rear portion of the stopper that radially expands the stopper thereby increasing an interference fit with an inner surface of the reservoir. Extension of the spring can impart a force to a rear portion of the stopper that radially contracts the stopper thereby reducing an interference fit with an inner surface of the reservoir. The spring can provide an injection force at about 30% compression of the spring or less that exceeds a resistance force experienced by the stopper during translation within the reservoir. A rate of injection can be based upon an amount of compression of the spring.

In various aspects, the stopper can be advanced a predefined length into the reservoir by activation of the actuation mechanism. Advancing the stopper the predefined length can deliver a volume of the shape adaptable material in a range from about 0.01 μL to about 10 mL, or from about 0.1 μL to about 1 mL, or from about 1 μL to about 100 μL, or from 1 μL to about 20 μL. The predefined length can be in a range from about 0.25 mm to about 60 mm, or about 0.5 mm to about 10 mm, or about 1 mm to about 5 mm. Advancement of the stopper into the reservoir can be limited to a stop distance from a distal end of the reservoir prior to injection. The reservoir can have an axial length (L) and the stop distance can be about 9/10 of the axial length (0.9 L) or less. In some aspects, the stopper can be coupled to an end of the plunger. Force transmission between the stopper and the plunger can cause radial contraction of the stopper. Force transmission between stopper and plunger can cause radial expansion of the stopper. The stopper can be coupled to the plunger via a prong and a complementary cavity of the stopper. A length of the prong can be greater than a length of the complementary cavity. Extension of the prong into the complementary cavity can radially contract the stopper thereby decreasing an interference fit with an inner surface of the reservoir. A length of the prong can be less than a length of the complementary cavity. A face of the plunger can contact the stopper during translation of the plunger, and the contact can axially compress and radially expand the stopper thereby increasing an interference fit with an inner surface of the reservoir. The stopper can be an integrated part of the plunger. The stopper can comprise material having a shore hardness in a range from 0A to about 90A. The shore hardness can be in a range from about 30A to about 75A. The stopper can comprise material having a tensile modulus at 100% strain in a range from about 0.1 MPa to about 10 MPa. The tensile modulus can be in a range from about 1 MPa to about 4 MPa.

In many aspects, the actuation mechanism can pneumatically force the stopper into the reservoir. The stopper can maintain an effective static seal by radially expanding in response to the pneumatic force applied to the stopper. The actuation mechanism can release a fluid to apply the pneumatic force to the stopper. The actuation mechanism can comprise one or more elements which are manually manipulated to force the stopper into the reservoir. The one or more elements can comprise gears that translate rotation to axial movement of the stopper in the reservoir. The actuation mechanism can comprise one or more elements which are deformed to expand in the axial direction to force the stopper into the reservoir. In one or more aspects, the shape adaptable material can comprise a non-Newtonian material. The shape adaptable material can have a viscosity of less than 5000 cp. The shape adaptable material can be compounded for elution of a drug, biological, or therapeutic substance. A volume of the shape adaptable material present in the reservoir can be about 110% to about 1000% of an injection volume delivered by the injection device. The injection volume can be in a range from about 0.1 μL to about 250 μL. In some aspects, reservoir geometry can enable purging of air from the reservoir during introduction of the stopper and formation of a seal with the stopper. The reservoir can have a geometry that facilitates uniform fluid flow of the shape adaptable material through the injection port as the stopper is forced into the reservoir. The junction component can comprise a dispensing channel extending between a distal end of the reservoir and the injection port. The dispensing channel can comprise an intermediate chamber at the distal end of the reservoir. The intermediate chamber can have a barrel diameter in a range of about 25% to about 95% of a barrel diameter of the reservoir. A transition between the reservoir and the intermediate chamber can have a curvature of radius of about 20% to about 100% of the barrel diameter of the intermediate chamber.

In various aspects, the reservoir and seals made by the stopper and injection port cover can mitigate fluid or gas transmission into or from the reservoir. The junction component, stopper, and/or injection port cover can be fabricated with low permeability materials with a water diffusion coefficient of about $1\times10^{-6}$ $cm^2/s$ or less or a moisture vapor transmission rate of about 10 $g/m^2/day$ or less. The junction component can comprise glass, metal, cyclic olefin polymers or copolymers, or cyclic olefin or metal compounded or layered materials. The stopper can comprise fluorocarbon, fluoroelastomer, or rubber. The injection port can comprise an injection port tube extending from the junction component. The injection port tube can be configured to deliver the shape adaptable material into a tear duct. The injection port tube can comprise a blunt tip. The shape adaptable material can change properties to form an occlusive plug in the tear duct. The shape adaptable material can change from a flowable liquid to a more viscous liquid or solid. The injection port tube can have an outer diameter in a range from about 0.3 mm to about 1.5 mm. The injection port tube can have a length in a range from about 0.5 mm to about 10 mm. The injection port tube can comprise polycarbonate, PEEK, polyimide, PEBAX, or stainless steel. The shape adaptable material can be a polymer hydrogel. The polymer hydrogel can comprise a NIPAM (N-lsopropylacrylamide) monomer. The polymer hydrogel can comprise one or more additional monomers. The polymer hydrogel can comprise a cross-linking monomer or excipient. The injection port can have a ratio of wall thickness to length of about 0.005. The injection port can have a ratio of barrel diameter to length in a range from about 1:1000 to about 4:1. The reservoir can comprise a cavity configured to contain a predefined volume of the shape adaptable material. The injection device can be a disposable device with the reservoir prefilled with the predefined volume of the shape adaptable material. The junction component can be a disposable component with the reservoir prefilled with the predefined volume of the shape adaptable material. The body and actuation mechanism can be reusable.

In many aspects, the injection device can comprise an activation trigger configured to activate the actuation mechanism. The activation trigger can comprise a button configured to engage with the plunger. The button can arrest the plunger and stopper combination at a position in the reservoir where the position determines a defined volume of the shape adaptable material for injection. The activation trigger can comprise a lever configured to activate the actuation mechanism. The body can encase the actuation mechanism, and the body can be sized to fit in a user's hand. In one or more aspects, a replaceable cartridge can be connected to the reservoir or act as the reservoir, the replaceable cartridge containing the shape adaptable material. The replaceable cartridge can be the junction component comprising a seal at both ends. The junction component can be integrated in the body. The junction component can comprise polycarbonate, polypropylene, polyvinyl chloride, PET, PETG, cyclic olefin polymers or copolymers, or cyclic olefin or metal compounded or layered materials, or other plastics, metal, or glass, or other materials which may be used in fabrication. The stopper and/or injection port cover can comprise fluorocarbon, fluoroelastomer, rubber, silicone, urethanes, TPE, or TPVs, and/or other flexible materials. In some aspects, the reservoir can be prefilled with an injection volume of the shape adaptable material in a range from about 0.01 μL to about 1 mL. At least 90% of the injection volume can be delivered to a target location within a predefined time of activation of the injection device. The predefined time can be about 5 seconds or less. The injection volume can be in a range from about 0.1 μL to about 250 μL. The reservoir can contain a volume greater than the injection volume. The volume contained by the reservoir can be about 5% to about 2000% more than the injection volume. The shape adaptable material can comprise a polymer hydrogel comprising a concentration of 0.2% to 70% polymer or copolymer. The shape adaptable material can have a viscosity of 5000 cp or greater. The injection device can be configured to provide an indication of integrity or readiness of the shape adaptable material or the injection device. The junction component can be optically translucent or transparent. The injection device can comprise radiation compatible materials suitable for a cumulative radiation dose of about 100 kGy or less. The junction component can comprise an activatable heating or cooling element for conditioning of the shape adaptable material before injection. The reservoir can comprise a barrier configured for removal allowing a combination of substances to be mixed prior to injection. The combination of substances can form the shape adaptable material.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the disclosed aspects, as well as all optional and preferred features and modifications are combinable and interchangeable with one another.

The advantages will be set forth in part in the description which follows, and in part will be obvious from the description, or may be learned by practice of the aspects described below. The advantages described below may be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below:

FIG. 2 is a table illustrating components of an injection device, in accordance with various embodiments of the present disclosure.

DETAILED DESCRIPTION

Figure 1:
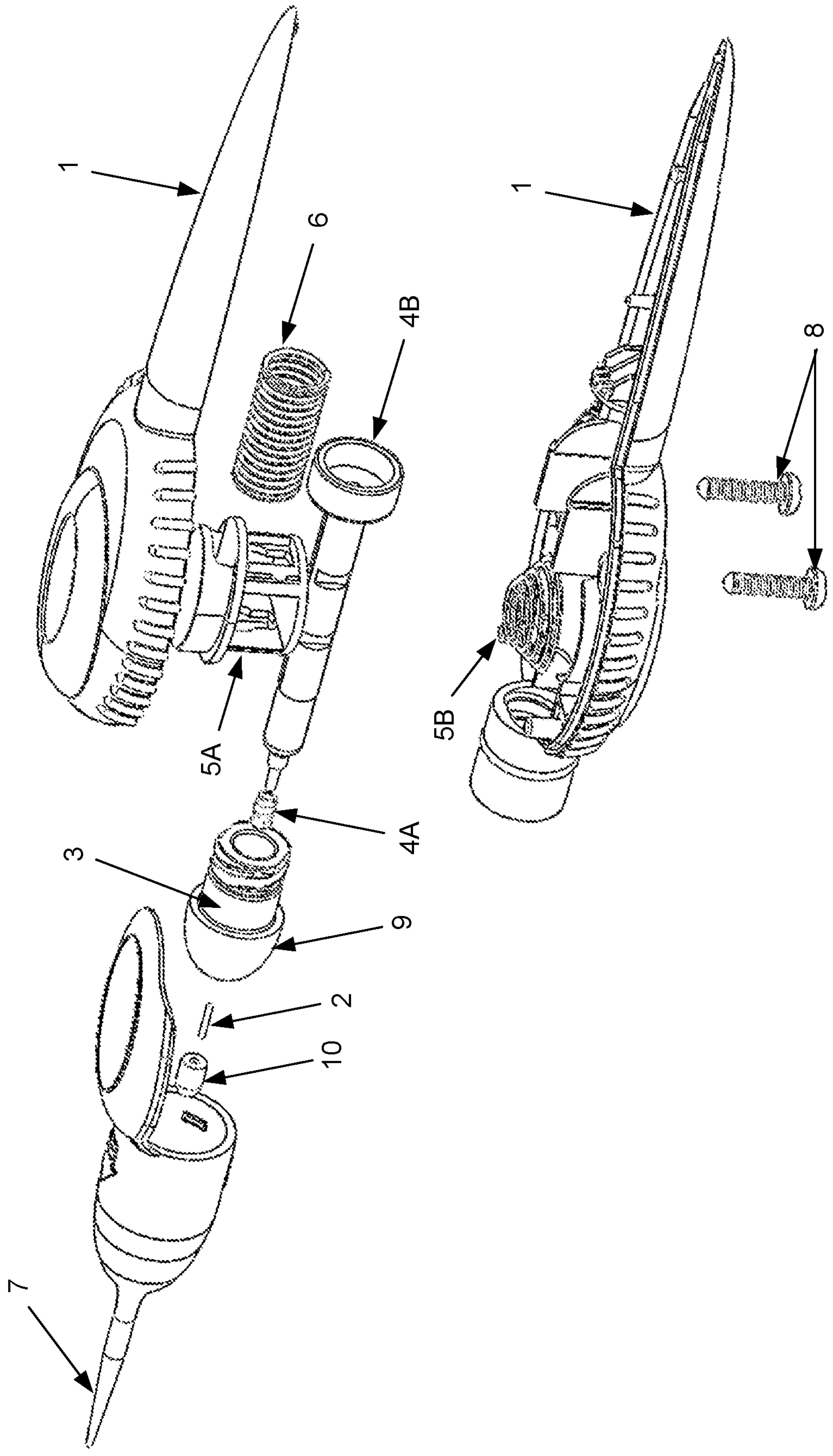
FIG. 1 illustrates an example of an injection device in various perspective views, in accordance with various embodiments of the present disclosure. This embodiment utilizes a form of mechanical actuation, such that a pressurizing component is controlled by releasing a loaded compression spring in the axis of pressurization.

Many modifications and other embodiments disclosed herein will come to mind to one skilled in the art to which the disclosed compositions and methods pertain having the benefit of the teachings presented in the foregoing descriptions and the associated drawings.

Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method and/or construction can be carried out in the order of configurations recited or in any other order that is logically possible. That is, unless otherwise expressly stated, it is in no way intended that any method or aspect set forth herein be construed as requiring that its steps or construction be presented in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps, components, assembly, operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Geometries, kinetics, durations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an example, a numerical range of "about 1" to "about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, from about 1—about 3, from 1 to about 3, from about 1 to 3, etc., as well as 1, 2, 3, 4, and 5, individually. The same principle applies to ranges reciting only one numerical value as a minimum or maximum. The ranges should be interpreted as including endpoints (e.g., when a range of "from about 1 to 3" is recited, the range includes both of the endpoints 1 and 3 as well as the values in between). Furthermore, such an interpretation should apply regardless of the breadth or range of the characters being described.

Disclosed are components, mechanisms, and materials that can be used for, can be used in conjunction with, can be used in preparation for, or are products of the disclosed configurations and methods. These and other components are disclosed herein, and it is understood that when combinations, subsets, interactions, groups, etc. of these components are disclosed, that while specific reference to each various individual combination and permutation of these components may not be explicitly disclosed, each is specifically contemplated and described herein. For example, a type of mechanism is disclosed and discussed, and a number of different components are discussed, each and every combination of mechanisms and components that is possible is specifically contemplated unless specifically indicated to the contrary. For example, if a class of mechanisms A, B, and C are disclosed, as well as a class of components D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, components, configurations, mechanisms, assemblies, constructions, and methods using the disclosed mechanical features. Thus, if there are a variety of additional configurations that can be performed with any specific embodiment or combination of embodiments of the disclosed methods, each such configuration is specifically contemplated and should be considered disclosed.

In the specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a mechanism" or "a component" includes combinations of two or more mechanisms or components and the like.

"Optional" or "optionally" means that the subsequently described event or circumstance can or cannot occur, and that the description includes instances where the configuration or circumstance manifests and instances where it does not.

Throughout this specification, unless the context dictates otherwise, the word "comprise," or variations such as "comprises" or "comprising," will be understood to imply the inclusion of a stated element, integer, step, feature, or group of elements, integers, steps, or features, but not the exclusion of any other element, integer, step, features, or group of elements, integers, steps, or features.

As used herein, the term "about" is used to provide flexibility to a numerical range endpoint by providing that a given numerical value may be "a little above" or "a little below" the endpoint without affecting the desired result. For purposes of the present disclosure, "about" refers to a range extending from 10% below the numerical value to 10% above the numerical value. For example, if the numerical value is 10, "about 10" means between 9 and 11 inclusive of the endpoints 9 and 11.

As used herein, the term "inject"—and its grammatically inferred arrangements—may refer to any action in which a material is physically transferred from a device into a site or location of interest and may be considered as interchangeable with similarly descriptive verbiage, such as delivered, applied, dispensed, and the like, unless otherwise specified to take on a specific or significant distinction.

As used herein, the term "bolus" may refer to any substance which could conceivably be transferred by cannula or outlet from a reservoir into a location of interest and may be considered as interchangeable with similarly descriptive verbiage in the appropriate context, such as fluid, solution, formulation, liquid, gel, polymer hydrogel, hydrogel, material(s), substance, and the like, unless otherwise specified to take on a specific or significant distinction.

As used herein, the term "applicator" may refer to any complete assembly that dispenses a bolus and may be considered as interchangeable with similarly descriptive verbiage, such as dispenser, injector, injection device, device, delivery system, and the like, unless otherwise specified to take on a specific or significant distinction.

As used herein, the term "dose" or "dosage" may refer to either the intended injection volume and/or mass, concentration of a specific ingredient, or similar empirically measurable parameters.

As used herein, the term "reservoir" may to refer to a cavity wherein a fluid is held at the moment prior to injection. In some cases, the term is used interchangeably with words such as barrel, however there may also be some distinction between these terms when used within the same description of a feature; for example, the reservoir may be the entirety of the substance containing geometry, while the barrel is the segment which makes contact with the stopper. Further, reservoir and barrel can be a feature present within another component, like the hub, and in such cases can often be referred to interchangeable as well. The reservoir or components comprising the reservoir can be optically translucent or transparent to enable visual verification of preservation of material properties of a contained substance and of device readiness for use.

As used herein, the term "injection port" may refer to any outlet or channel through which a bolus is ejected and may be considered as interchangeable with similarly descriptive verbiage, such as needle, tip, cannula, tube, outlet, dispensing port, dispensing site, and the like, unless otherwise specified to take on a specific or significant distinction. While discussion of particular applications, such as that for dry eye, imply the benefit of a blunt-ended injection port, such an example should not be considered as excluding the use of the injection port as a subcutaneous, or otherwise, sharp-ended delivery system, in particular, but not exclusively, for pharmaceutical applications.

As used herein, the term "hub" may refer to any component(s) that serves as a container and/or joint for one or more components or features directly responsible for injection, particularly including the reservoir and the injection port. The hub may also serve to connect the features to the body and actuating elements. Further, the hub may often refer to the feature which determines the depth of the injection port by acting as the physical interface and limiter based on an exposed length of the joined component in question. "Hub" may be considered as interchangeable with similarly descriptive and representative verbiage, such as junction component, interface, joint, cartridge, barrel, limiter, reservoir (when appropriate), and the like, unless otherwise specified to take on a specific or significant distinction.

As used herein, the term "pressurization components" may refer to any component(s) or assembly that are directly responsible for pressurizing a reservoir. This may include a stopper and plunger, as defined below, but should also be understood to apply within the broad scope of possibilities discussed throughout this document.

As used herein, the term "stopper" may refer to any component or feature that acts upon a reservoir, directly causing an increase in pressure that initiates fluid dispensing and may be considered as interchangeable with similarly descriptive verbiage, such as, compressor, and the like, unless otherwise specified to take on a specific or significant distinction.

As used herein, the term "plunger" may refer to any actuating component or rigid member that receives an external force and acts upon the stopper to perform injection and may be considered as interchangeable with similarly descriptive verbiage, such as shaft, rod, lead screw, cam, spring, compressor, and the like, unless otherwise specified to take on a specific or significant distinction.

Note that in some cases, 'plunger' and 'stopper' may be the same component, referring to any geometry that interfaces with the channels and compartments of the fluid reservoir and through which movement of this interface creates a reduction in volume and an increase in pressure. In any context where one, both, or a combination of these components performs this function, they may be referred to (individually or collectively) and considered interchangeable with verbiage such as pressurization component(s), compressor, stopper, plunger, and the like, as applicable, unless otherwise specified to take on a specific or significant distinction.

As used herein, the term "body" may refer to any component(s) comprising the outer surfaces imparting structural integrity and general shape to the assembly while containing some or all of the other components within this shell so that they are not exposed. "Body" may be considered as interchangeable with similarly descriptive verbiage, such as frame, shell, and the like, unless otherwise specified to take on a specific or significant distinction.

As used herein, the term "activation trigger" may refer to any component(s) that receives external force or a specific signal initiated by the user, thus precipitating the events responsible for actuating injection. This should further be extended to include components that support or enable the actual component receiving the force to do so in an effective manner. "Activation trigger" may be considered as interchangeable with similarly descriptive and representative verbiage, such as button, switch, trigger, dial, valve, spring, guide and the like, unless otherwise specified to take on a specific or significant distinction.

As used herein, the term "actuation mechanism" may refer to any component(s) that apply or transmit force into the component(s) responsible for pressurizing the reservoir. "Actuation mechanism" may be considered as interchangeable with similarly descriptive and representative verbiage, such as actuator, spring, lever, cam, compressed gas, linear screw, worm gear, and the like, unless otherwise specified to take on a specific or significant distinction. Actuation mechanism may also refer to the mode of force generation as well as the mode of force transmission, collectively.

As used herein, the term "securing components" may refer to any component(s) that hold one or more components together, allowing them to form a strong joint, frame, and/or mate for transmission of force. "Securing components" may be considered as interchangeable with similarly descriptive and representative verbiage, such as screw, snap-fit, press-fit, latch, clasp, and the like, unless otherwise specified to take on a specific or significant distinction.

As used herein, the term "injection port cover" may refer to any component(s) that sit directly over the injection port, and which may further create a seal to prevent leakage or ingress of external substances, including, but not limited to air and water. An example of the use of this component is illustrated in FIGS. 11C and 11D. This component is distinct from a cap, which only provides protection from external forces, however, in some embodiments, the injection port cover may itself have a rigid exterior surface which provide protection to the encapsulated contents and/or a user and patient. "Injection port cover" may be considered as interchangeable with similarly descriptive and representative verbiage—including all variations of injection port—such as soft plastic (e.g. rubber) cover, seal, port/cannula/needle shield, and the like, unless otherwise specified to take on a specific or significant distinction.

As used herein, the term "dilator" may refer to any component(s) that perform the function of dilating, opening, or widening an injection site. In relation to some aspects, but not all, this feature is integrated into a protective cap, which protects or covers sensitive components which require exposure at the time of use. For the purposes of this document, "dilator" may be considered as interchangeable with similarly descriptive and representative verbiage, such as cap, dilator cap, punctal dilator, and the like, unless otherwise specified to take on a specific or significant distinction.

As used herein, the term "injection efficiency" may refer to the proportion of volume or mass of fluid that is successfully dispensed compared to the total volume or mass of fluid that was present in the fluid reservoir from which it was ejected prior to injection. In some instances, particularly those wherein the intention is not to deliver all or even most of the fluid within the reservoir, injection efficiency may be considered to mean the ratio between the actual injected mass or volume and the theoretical injection mass or volume.

As used herein, the term "occlusion efficiency" may refer to the proportion of cross-sectional area of a channel that is securely blocked by an injected material compared to the total cross-sectional area of that channel.

As used herein, the term "subject", "individual", or "patient" as used herein includes mammals. Non-limiting examples of mammals include humans, rabbits, pigs, dogs, cats, and mice, including transgenic and non-transgenic mice. The methods described herein can be useful in both human therapeutics, pre-clinical, and veterinary applications. In some embodiments, the subject is a mammal, and in some embodiments, the subject is human.

As used herein, the term "shape adaptable materials" and comparable terms may refer to any substance dispensed by a device, which forms, partially or completely, to the shape of the delivery site. Bolus, as defined above, may include these materials. Such substances include, but are not limited to liquids, gels, elastomers, hydrogels and other aqueous solutions, gases, vapors, pastes, putties, and multi-phase and property changing materials. For example, the shape adaptable material can be a NIPAM (N-Isopropylacrylamide) based hydrogel comprising a concentration of 0.2% to 70% polymer.

Often throughout this disclosure—and particularly with respect to the applicator for dry eye—the shape adaptable material can be a responsive substance which fills a channel (e.g., a tear duct) before changing properties to become an occlusive plug. As another example, the shape adaptable material can be compounded for elution of a drug, biological, or other therapeutic substance. The fluids and materials can be biocompatible and/or medical grade components. Examples of various fluids or materials that can be utilized with the disclosed injection devices are provided in U.S. Patent Pub. No. 2018/0360743 ("Thermoresponsive Polymers and Uses Thereof" by Bartynski et al.), which is hereby incorporated by reference in its entirety.

Fundamental Construction and Injection Mechanisms

Described herein are mechanical arrangements for injecting a bolus for clinical, therapeutic, or commercial purposes, such as cosmetics or manufacturing implements. The preferred embodiment for this arrangement is that of a prefilled, single-use device, but this should not be construed as precluding reusable manifestations, as would be more common in non-medical applications. When actuation is triggered, the bolus undergoes pressurization within the device or, in some embodiments, a cartridge. The preferred embodiment for this arrangement is that pertaining to a single trigger, instantaneous bolus ejection, but this should not be construed as precluding manifestations with capability for variable dosage.

An embodiment of the device is shown in FIG. 1. This example utilizes a form of mechanical actuation, such that a pressurizing component is controlled by releasing a loaded compression spring in the axis of pressurization. FIG. 2 is a table providing a description of the components. As seen in FIG. 1, the embodiment comprises two halves of the body, which can contain the components utilized for performing an injection: a depressible button (5A), which is exposed and approximately level with the surface of the body (1), rests atop a conical spring (5B) and constrains a plunger (4B). The plunger (4B) is under compression from a spring (6) in the longitudinal axis. The body halves (1) are secured together using screws (8). Further, this embodiment comprises a junction component (9) that connects both to the main body (1) and to the injection port tube (2). The junction component (9) has an internal geometry designed to be filled with injection fluid as well as a stopper (4A), which is separate from the plunger (4B) and which pushes the fluid out of the port during injection. Additionally, there is a soft plastic cover (10) that rests over the port tube (2) that is removed before injection, along with a cap (7) that snaps into place over top of the body (1), protecting the port tube (2) and covering the button (5A) to prevent accidental depression.

This attachment (7) or one segment of the body (1) may include a long, thin, conical extrusion which serves as a punctal dilation tool in the event that a physician determines that the pathway is too small or constricted.

In some aspects, the cap (7) may also be used to prevent unintended activation of the device by covering the part of the device where external force is required to perform injection.

The activation trigger comprises the depressible button (5A) described above, which is able to rest at one of two positions, depending on whether it is engaged or not. When disengaged, the button's surface rests approximately flush with the surface of the body (1) and the conical spring (5B) is subject to loading equal to the weight of the button (5A) and the reaction force of the button (5A) being constrained by the body (1). The geometry of the button (5A) in the device's primary longitudinal axis is designed to interlock with the plunger (4B), preventing it from moving along that axis. For example, one or more tabs of the button (5A) can extend through corresponding recesses of the plunger (4B) to secure the plunger and stopper (4A) in a first position. When engaged, the button (5A) further compresses the conical spring (5B). The geometry in this longitudinal axis changes with button depth and eventually becomes a shape such that the plunger component (4A) is able to pass through the button (5A) unobstructed. For example, the tabs of the button (5A) slide out of the corresponding recesses allowing the plunger (4B) and stopper (4A) to advance through one or more openings in the button (5A) to a second position. When engaged, the interlocking geometry of the components (4B and 5A) prevent the button (5A) from being reset by the conical spring (5B). The plunger (4B) is under constant loading from a compressed spring (6) which is housed within the body (1) and further constrained by the geometry of the plunger (4B) itself. For example, the plunger (4B) can include a recess at one end that is configured to receive one end of the spring (6) to prevent radial and transverse movement. When the feature (e.g., button 5A) preventing advancement of the plunger (4B) is displaced, the spring will unload or extend, causing the plunger (4B) to translate until either the free length of the spring (6) is met, or until the plunger (4B) reaches a hard stop. The plunger (4B) advances along the longitudinal axis and, if they are decoupled, the plunger (4B) makes contact with the stopper (4A), which is also pushed under direction of the internal geometry of the hub (9). If the stopper (4A) and plunger (4B) are coupled, then the pressurizing component(s) will move as a unit. The distal end of the stopper (4A) creates a seal against the internal geometry of the hub (9) as it advances into the reservoir (3), forcing the fluid to escape the distal end of the hub (9) into and out of the injection port tip (2). In this embodiment, the injection occurs rapidly (or nearly instantaneously), but this is not a requirement for operation of the device as a whole.

FIGS. 3-10 illustrate examples representing some alternate modalities of injection. Injection may be actuated by manual or mechanical means, including, but not limited to:

- Direct axial force on the plunger, or any component connected to the fluid reservoir, resulting in translation of such components and/or reservoir, such that their contained volumes encroach and overlap.
- Rotation of a gear—worm or otherwise—resulting in relative axial translation to act upon the plunger.
- Translation or rotation of a lever, ramp, cam style, or hinged component which obliquely and gradually applies force to the plunger in the axis of pressurization.
- Translation, compression, or rotation of one or more components which cause itself or an interfering component to deform in the axis of pressurization, thus translating the plunger.
- Compression or expansion of a flexible cavity with a complete or partial seal and/or paired compartments such that the pressure resulting from a change in volume causes a corresponding pressure change on or around the plunger resulting in a translating force normal to the cross-sectional area exposed to the pressure change; this can be gradual or cause binary movement upon reaching a particular threshold.
- Release of fluid or compressed gas—either gradually or in a burst—to fill a cavity and act upon a plunger (as described above), or act directly upon the fluid in the reservoir.
- Release of compressed spring(s)—either gradually or in a burst—acting upon a plunger.
- Expansion, contraction, or reshaping of responsive materials, such as nitinol, gases, or foams.
- Repulsion or attraction by exposure of magnetic forces or application of electrical impulse.

In some aspects, the reservoir may be under constant pressure wherein injection is achieved by removing a boundary between the reservoir and the outlet, such that a seal is in place at the joint of boundary removal to prevent passage anywhere but through the intended outlet. In some aspects, this method may be used in a cyclical fashion, thus metering the outflow and effectively controlling the average injection speed over time.

While this disclosure pays special mind to low-volume applications and those using high viscosity materials (e.g., >2000 cp), due to the necessity of innovation with regard to challenges of sensitivity and precision, in particular, but not exclusively, this should not be construed as precluding any embodiment of the disclosure from being applied to the application of greater volumes or lower viscosities. In spirit, the embodiments of this disclosure are scale-modular and property agnostic, meaning they are considered applicable in manifold ranges of scale and material viscosities.

The structural functionality of the body can also be a factor in the efficient design of an injection device. In some aspects, the internal geometries form structures that serve to strengthen and support the device against external forces. In some aspects, these structures also serve to align internal assembly components with one another, such as placement of an activation button, and provide a grounding for components involved in actuation, such as a backboard for a spring. Further, in some aspects, the body exists as the joining of two halves, which better allows for assembly installation and which may be secured together by features within the body, such as screw slots and snap fit mates.

Figure 3:
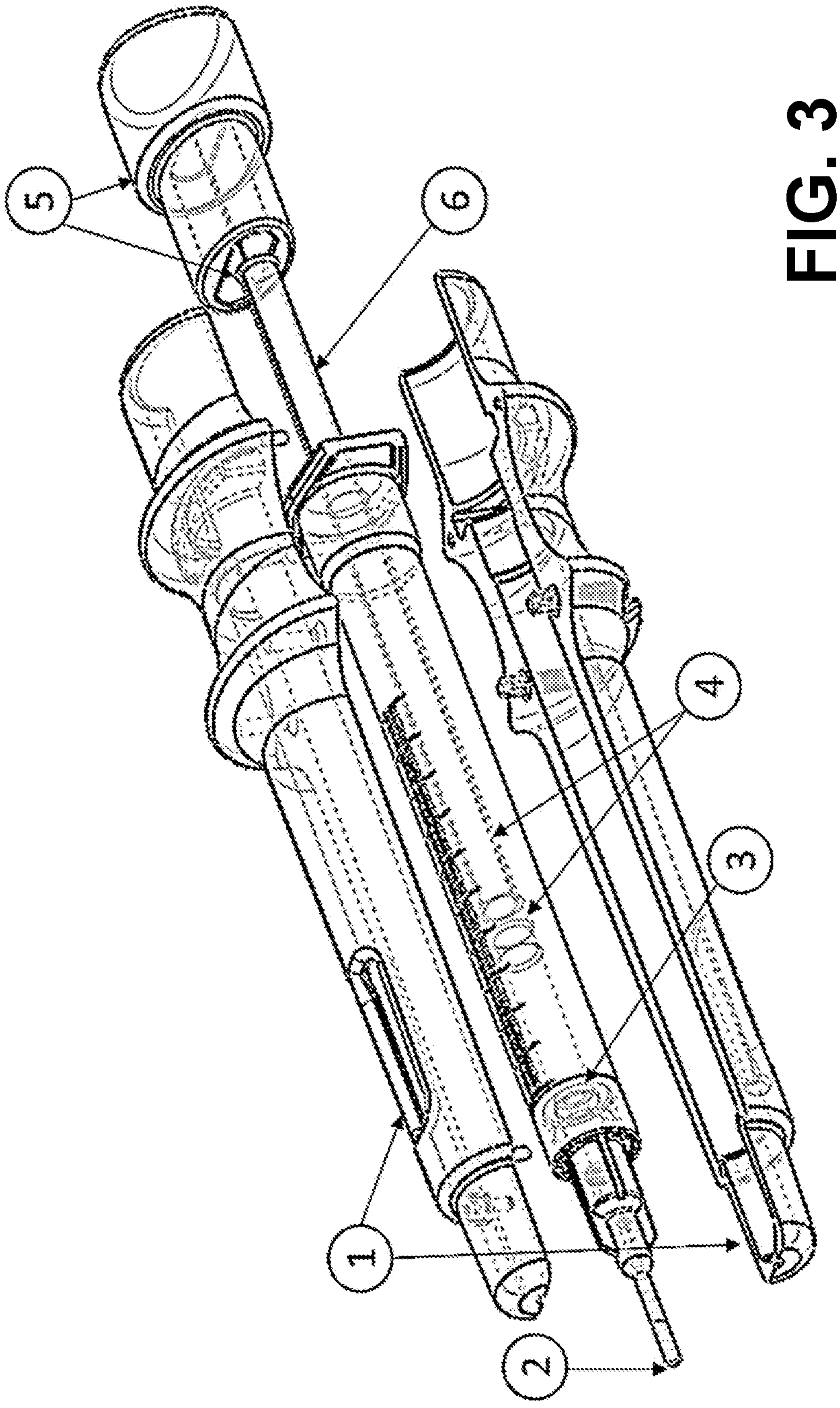
FIG. 3 depicts another example of an injection device in exploded perspective view, in accordance with various embodiments of the present disclosure. This embodiment utilizes a manual method of actuation, such as the use of a depressed plunger.

Referring to FIG. 3, shown is an example of an injection device that utilizes a manual method of actuation, such as the use of a depressed plunger. The body (1) may comprise one or more components designed to form or to house a reservoir (3), while providing a functional shape for manual manipulation. A plunger, which may provide portions of both the activation mechanism (5) and the actuation mechanism (6), may be directly manipulated, or may receive an input force from some form of attachment (5) intended to simplify, increase stability, limit travel, and/or provide greater comfort to the user. A stopper (4) at the end of the plunger can be gradually depressed to pressurize the reservoir (3), causing the fluid within the reservoir to evacuate through the dispensing port (2), which may be part of an attachment, or may be an integrated element within the body (1). A hub, or interfacing component, is also contemplated as described in the table of FIG. 2, but is not illustrated in FIG. 3.

Figure 4:
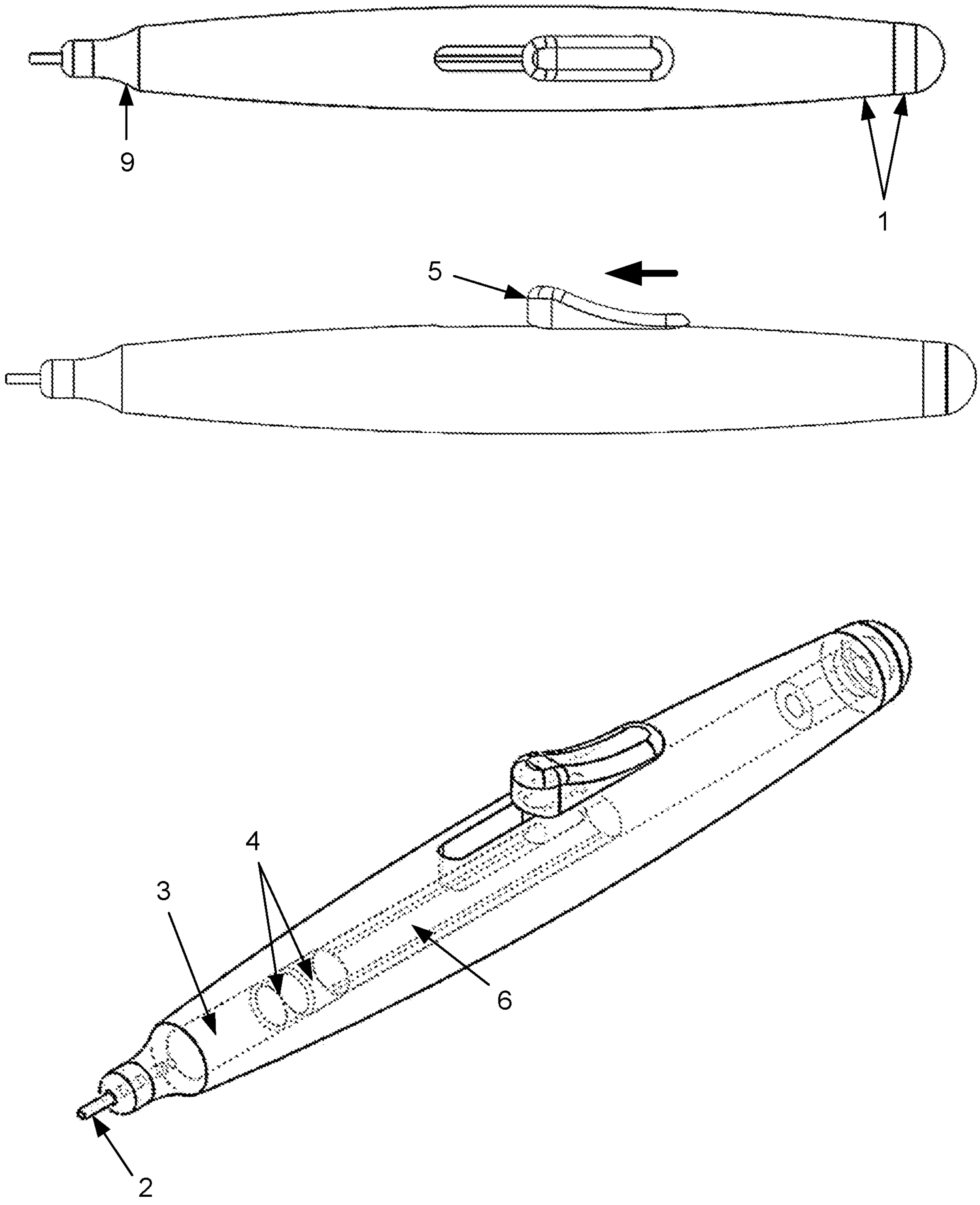
FIG. 4 illustrates another example of an injection device in various perspective views, in accordance with various embodiments of the present disclosure. This embodiment utilizes another form of manual actuation, such that a pressurizing component is controlled via a sliding movement.

Referring to FIG. 4, shown is an example of an injection device that utilizes another form of manual actuation, such that a pressurizing component is controlled via a sliding movement. The body (1) may comprise one or more components designed to form or to house a reservoir (3), while providing a functional shape for manual manipulation. A plunger, which may provide portions of both the activation mechanism (5) and the actuation mechanism (6), may be directly manipulated, or may receive the input force from some form of attachment (5) intended to simplify, increase stability, limit travel, and/or provide greater comfort to the user. In some aspects, the plunger and the force—or slide—input component(s) are not a singular element, but instead the force/slide input element can also include a locking mechanism, such that depression or toggling of the element is needed before the element, connected to the plunger, can be translated. A stopper (4) at the end of the plunger can be gradually depressed to pressurize the reservoir (3), causing the fluid within to evacuate through the dispensing port (2), which may be part of a hub (9) attachment, or may be an integrated element within the body (1).

Figure 5:
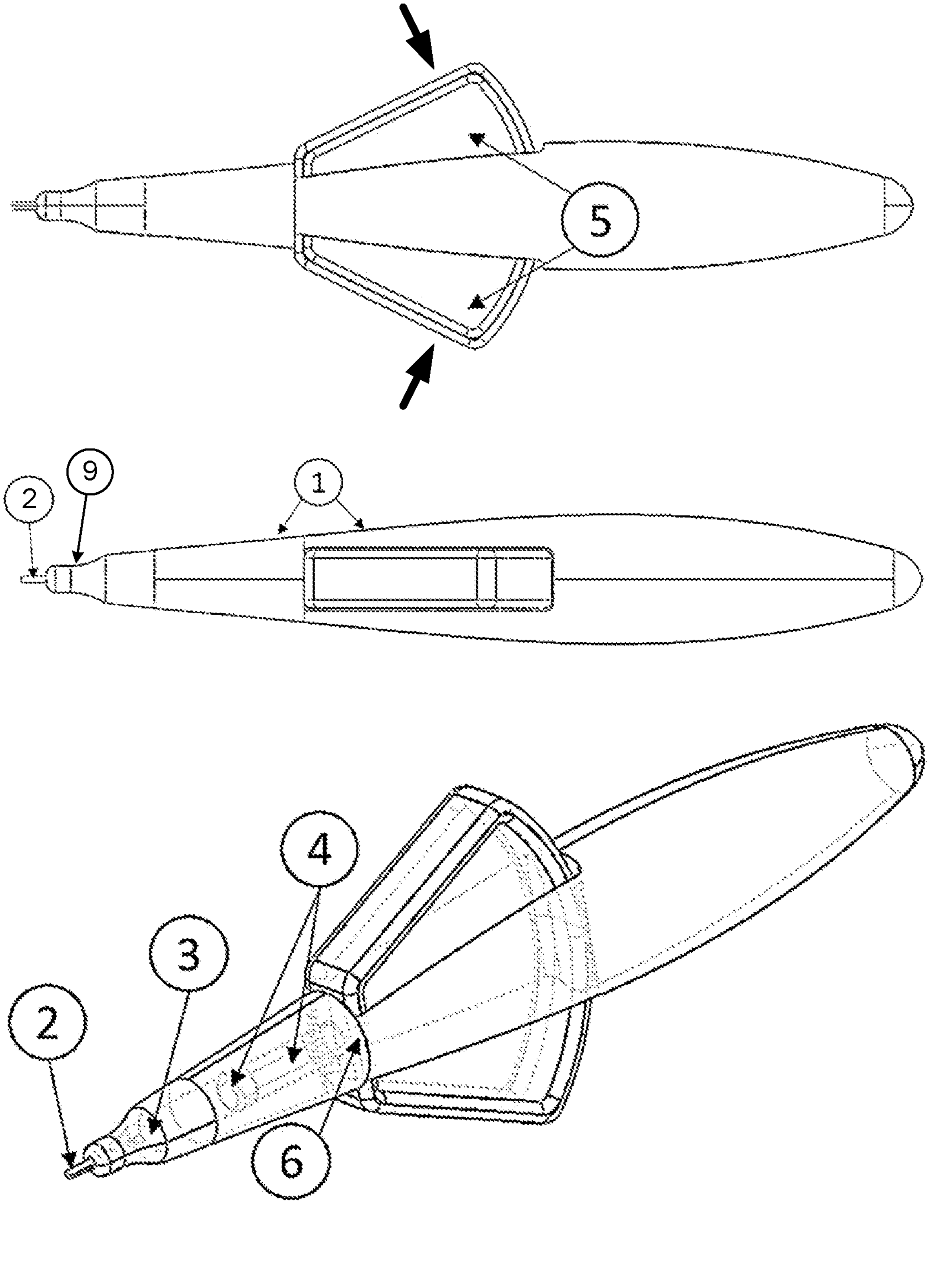
FIG. 5 depicts another example of an injection device in various perspective views, in accordance with various embodiments of the present disclosure. This embodiment utilizes a form of mechanical actuation, such that one or more rotating levers are squeezed to control a pressurizing component.

Referring to FIG. 5, shown is an example of an injection device that utilizes a form of mechanical actuation, such that one or more rotating levers are squeezed to control a pressurizing component. The body (1) may comprise one or more components designed to form or to house a reservoir (3), while providing a functional shape for manual manipulation. One or more lever or trigger elements (5) can be raised from the surface of the body (1) and provide purchase for the user to apply activation force. In some aspects, the activation mechanism (5) can interact directly with the actuation mechanism (6), e.g., the plunger and/or stopper (4). For example, the activation mechanism (5) can cause movement of intermediary components which themselves cause translation of the plunger, or which may cause a release of potential energy axially (e.g., from a spring). In some implementations, the levers can have a shape which causes their inward movement to directly move the plunger axially. In other implementations, the inward movement can cause an element to deflect in the axis of translation. The stopper (4) at the end of the plunger can be depressed to pressurize the reservoir (3), causing the fluid within to evacuate through the dispensing port (2), which may be part of a hub (9) attachment or may be an integrated element within the body (1).

Figure 6:
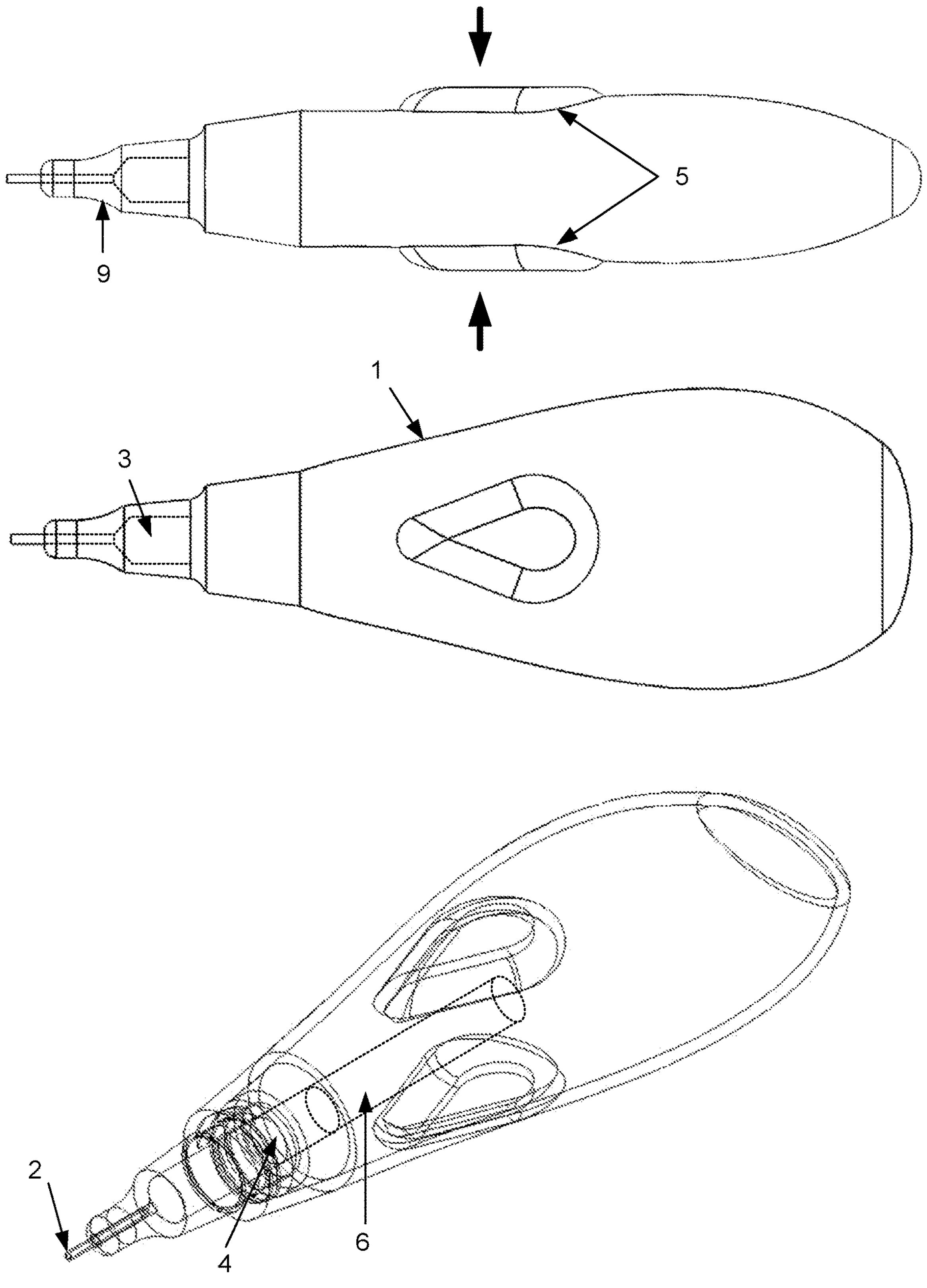
FIG. 6 shows another example of an injection device in various perspective views, in accordance with various embodiments of the present disclosure. This embodiment utilizes a form of mechanical actuation, such that one or more depressible button(s) are squeezed to control a pressurizing component.

Referring to FIG. 6, shown is an example of an injection device that utilizes a form of mechanical actuation, such that one or more depressible button(s) are squeezed to control a pressurizing component. The body (1) may comprise one or more components designed to form or to house a reservoir (3), while providing a functional shape for manual manipulation. In some aspects, the activation mechanism (5) can include one or more depressible elements that can be raised from the surface of the body (1) and can provide purchase for the user to apply an activation force. In various aspects, the depressible element(s) may provide portions of both the activation mechanism (5) and the actuation mechanism (6), For example, the activation mechanism (5) can interact directly with a plunger and/or a stopper. In some implementations, the activation mechanism (5) can cause movement of one or more intermediary components which themselves cause translation of the plunger, or which may cause an axial release of potential energy (e.g., from a spring). For instance, the elements can have a shape which causes their inward movement to directly move the plunger axially. The inward movement can cause an element to deflect in the axis of translation. In some aspects, these elements and/or the body (1) can be deformable and may be squeezed to build up air (or other fluid) pressure within a container behind the plunger and/or stopper. A stopper (4) (e.g., at an end of a plunger) can then be depressed to pressurize the reservoir (3), causing the fluid within to evacuate through the dispensing port (2), which may be part of a hub (9) attachment, or may be an integrated element within the body (1).

Figure 7:
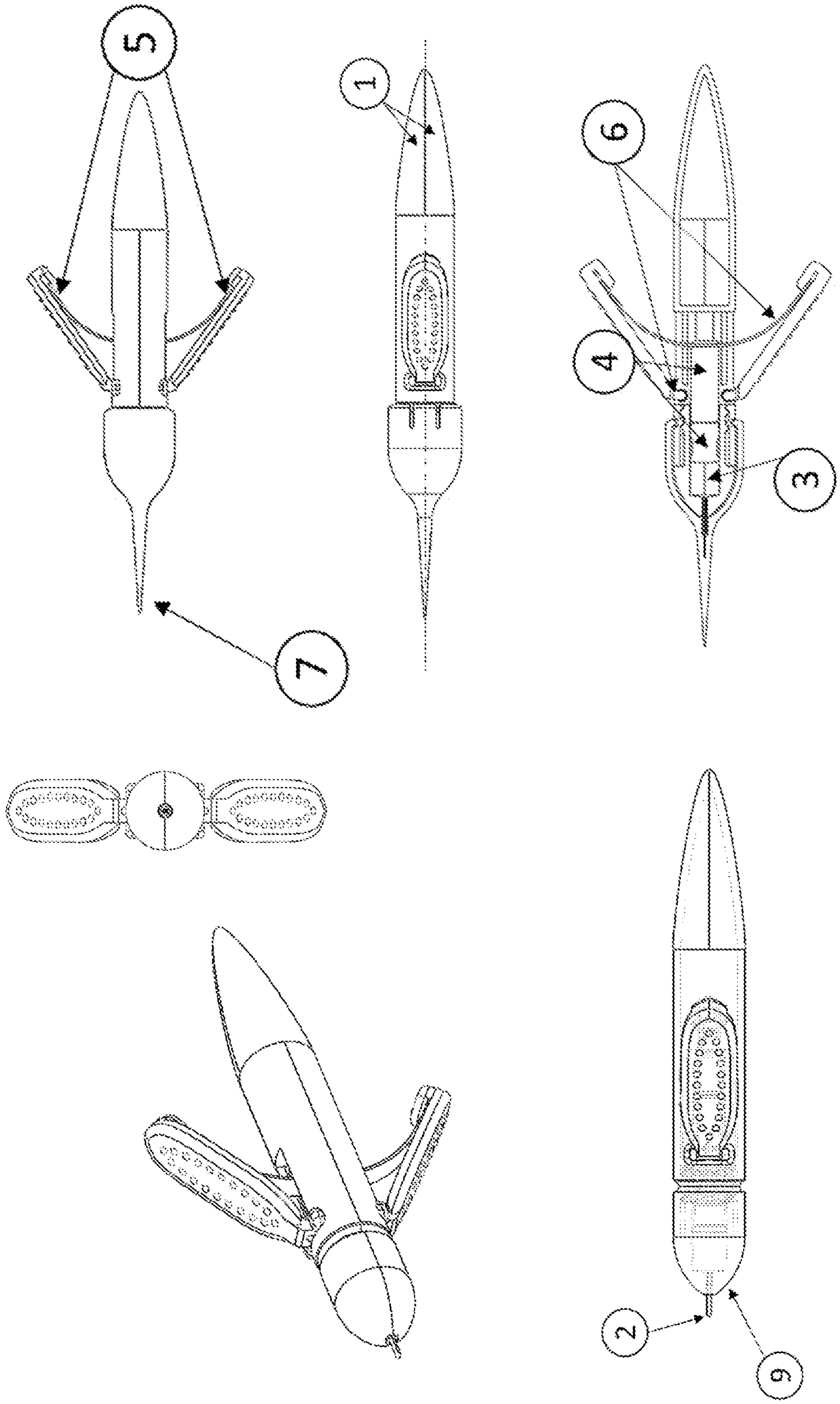
FIG. 7 shows another example of an injection device in various perspective views, in accordance with various embodiments of the present disclosure. This embodiment utilizes a form of mechanical actuation, such that one or more rotating lever(s) are used to incite deformation—either in some deformable feature of the lever(s) or in some connected component—in the axis of pressurization as a means of controlling injection.

Referring to FIG. 7, shown is an example of an injection device that utilizes a form of mechanical actuation, such that one or more rotating lever(s) are used to incite deformation—either in some deformable feature of the lever(s) or in some connected component—in the axis of pressurization as a means of controlling injection. The body (1) may comprise one or more components designed to form or to house a reservoir (3), while providing a functional shape for manual manipulation. The activation mechanism (5) can include one or more lever or trigger elements that can be raised from the surface of the body (1) and can provide purchase for the user to apply activation force. In some aspects, the activation mechanism (5) can interact directly with the plunger and/or stopper (4). For example, the activation mechanism (5) can cause movement of intermediary components which themselves cause translation of the plunger, or which may cause a release of potential energy axially (e.g. from a spring). In some implementations, the levers can have a shape which causes their inward movement to directly move the plunger axially. In some aspects, the inward movement can cause an element to deflect in the axis of translation. A stopper (4) at an end of the plunger can be depressed to pressurize the reservoir (3), causing the fluid within to evacuate through the dispensing port (2), which may be part of a hub (9) attachment, or may be an integrated element within the body (1).

Figure 8:
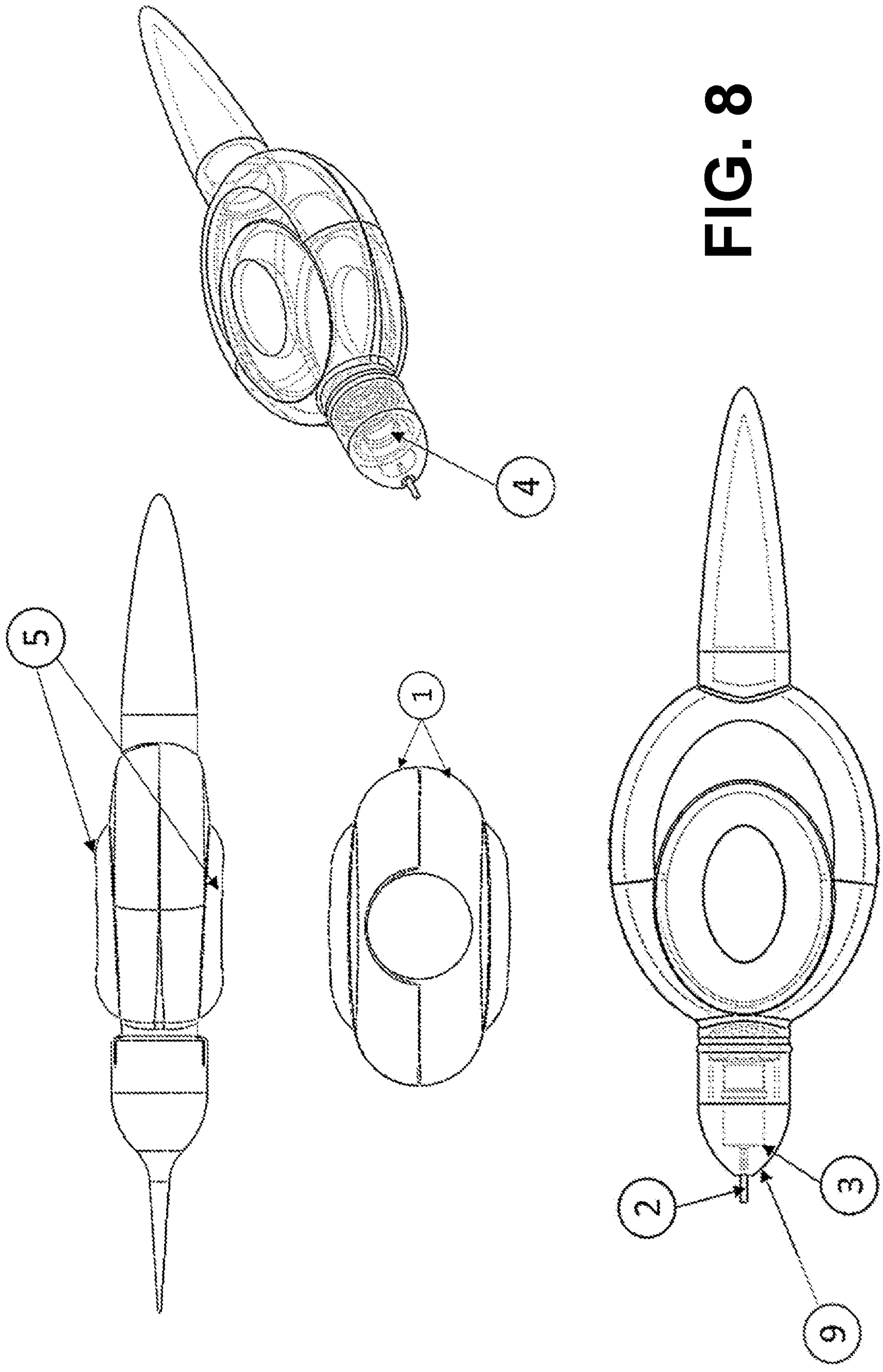
FIG. 8 shows another example of an injection device in various perspective views, in accordance with various embodiments of the present disclosure. This embodiment utilizes a form of mechanical actuation, such that a pressurizing component is controlled via squeezing movement on depressible button(s), deformable body, deformable button (s), or rotating lever(s).

Referring to FIG. 8, shown is example of an injection device that utilizes a form of mechanical actuation, such that a pressurizing component is controlled via squeezing movement on depressible button(s), deformable body, deformable button(s), or rotating lever(s). The body (1) may comprise one or more components designed to form or to house a reservoir (3), while providing a functional shape for manual manipulation. In some aspects, one or more depressible elements (5) are raised from the surface of the body (1) and provide purchase for the user to apply activation force. The depressible element(s) may provide portions of both the activation mechanism (5) and an actuation mechanism. In some aspects, the activation mechanism (5) can interact directly with a plunger and/or stopper. For example, the activation mechanism (5) causes movement of intermediary components which themselves cause translation of the plunger, or which may cause a release of potential energy axially (e.g., from a spring). In some aspects, the elements have a shape which causes their inward movement to directly move the plunger axially. In other aspects, the inward movement can cause an element to deflect in the axis of translation. In some aspects, these elements and/or the body (1) can be deformable and may be squeezed to build up air pressure within a container behind the plunger and/or stopper. The stopper (4) (e.g., at the end of the plunger) can be depressed to pressurize the reservoir (3), causing the fluid within to evacuate through the dispensing port (2), which may be part of a hub (9) attachment, or may be an integrated element within the body (1). A cap (7) can be included to cover and protect the injection end (e.g., the dispensing port) of the device.

Figure 9:
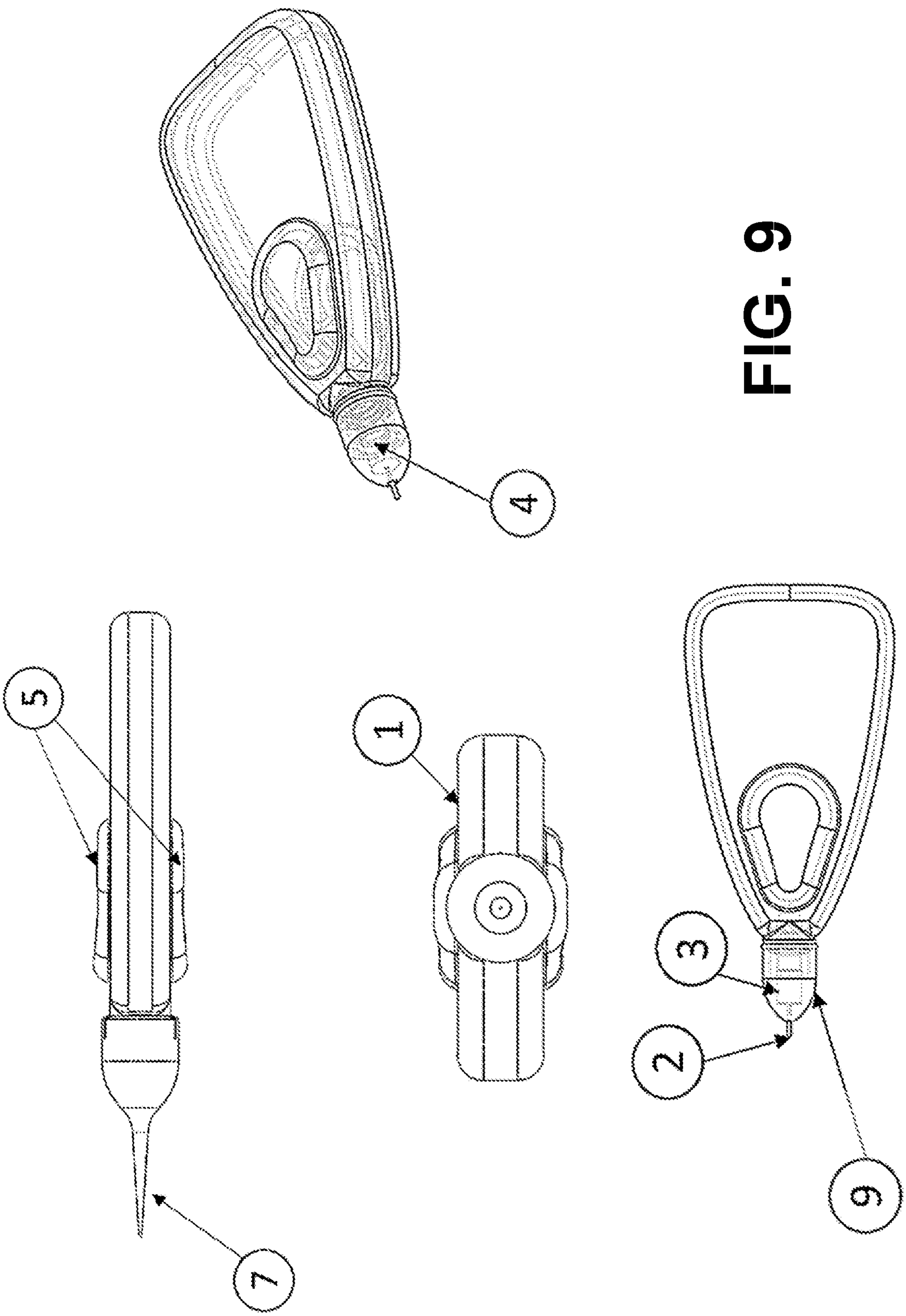
FIG. 9 shows an example of an injection device in various perspective views, in accordance with various embodiments of the present disclosure. This embodiment utilizes a form of mechanical actuation, such that a pressurizing component is controlled via squeezing movement on depressible button (s), deformable body, deformable button(s), or rotating lever (s).

Referring to FIG. 9, shown is an example of an injection device that utilizes a form of mechanical actuation, such that a pressurizing component is controlled via squeezing movement on depressible button(s), deformable body, deformable button(s), or rotating lever(s). The body (1) may comprise one or more components designed to form or to house a reservoir (3), while providing a functional shape for manual manipulation. In some aspects, one or more depressible elements (5) can provide purchase for the user to apply activation force. The depressible element(s) may provide portions of both the activation mechanism (5) and an actuation mechanism. In some aspects, the activation mechanism (5) can interact directly with a plunger and/or stopper (4). In some implementations, the activation mechanism (5) can cause movement of intermediary components which themselves cause translation of the plunger, or which may cause a release of potential energy axially (e.g., from a spring). In some aspects, the elements can have a shape which causes their inward movement to directly move the plunger axially. In other aspects, the inward movement can cause an element to deflect in the axis of translation. For example, these elements and/or the body (1) can be deformable and may be squeezed to build up air pressure within a container behind the plunger and/or stopper. The stopper (4) (e.g., at an end of the plunger) may be depressed to pressurize the reservoir (3), causing the fluid within to evacuate through the dispensing port (2), which may be part of a hub (9) attachment, or may be an integrated element within the body (1). A cap (7) can be included to cover and protect the injection end (e.g., the dispensing port) of the device.

Figure 10:
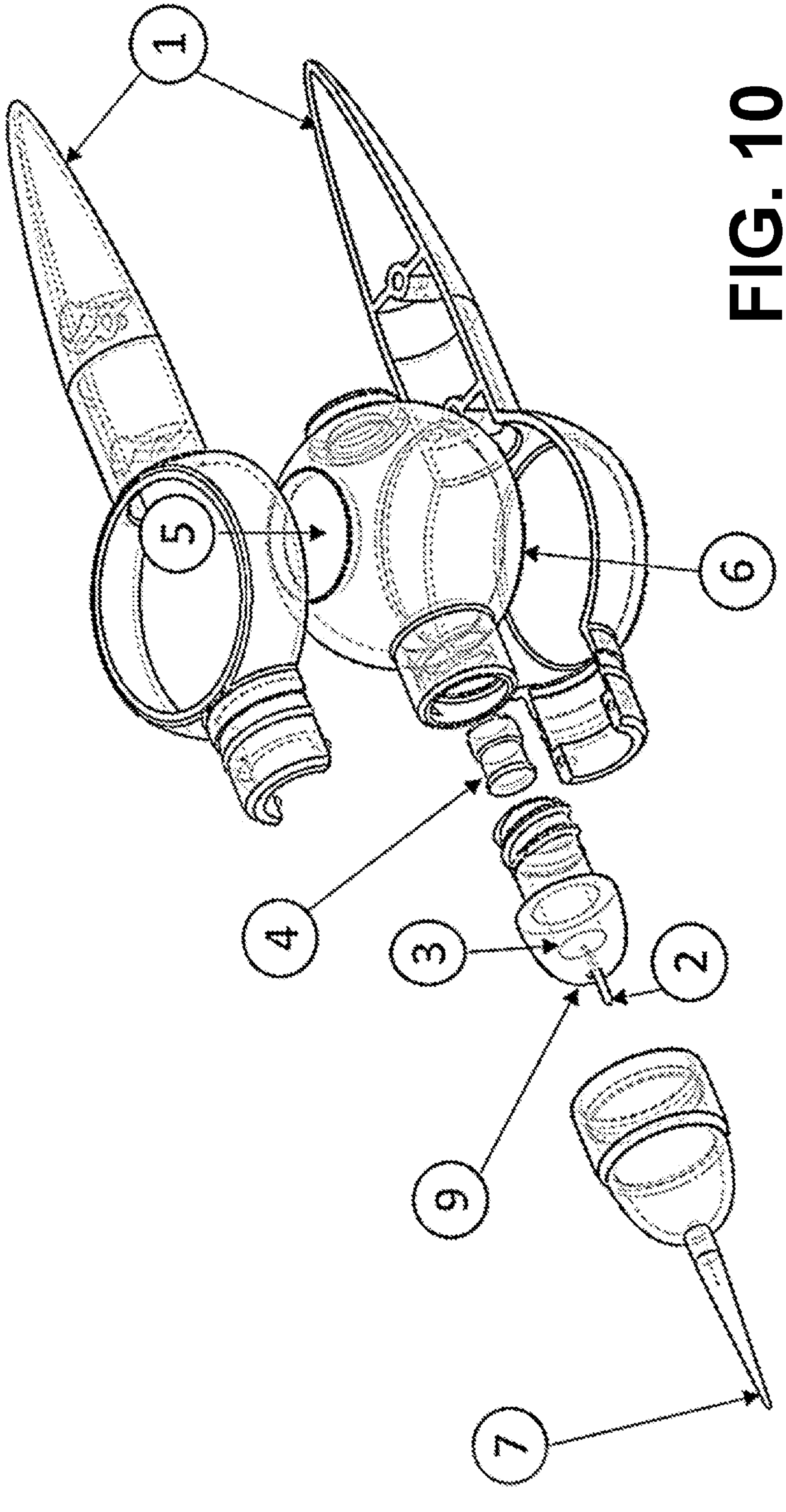
FIG. 10 depicts an example of an injection device in various perspective views, in accordance with various embodiments of the present disclosure. This embodiment utilizes a form of mechanical and/or pneumatic actuation, such that a pressurizing component is controlled by compressing a flexible bulbous component(s).

Referring to FIG. 10, shown is an example of an injection device that utilizes a form of mechanical and/or pneumatic actuation, such that a pressurizing component is controlled by compressing a flexible bulbous component(s). The body (1) may comprise one or more components designed to form or to house a reservoir (3), while providing a functional shape for manual manipulation. In some aspects, one or more depressible elements (5) provide purchase for the user to apply activation force. The depressible element(s) may provide portions of both the activation mechanism (5) and an actuation mechanism (6). For example, the activation mechanism (5) interacts directly with a plunger and/or stopper (4). In some aspects, the activation mechanisms cause movement of intermediary components which themselves cause translation of the stopper (4). In some aspects, the elements have a shape which causes their inward movement to directly move the stopper axially through pneumatic pressure. In some implementations, these elements and/or the body (1) can be deformable and may be squeezed to build up air pressure within a container behind the plunger and/or stopper. The stopper (4) can be depressed to pressurize the reservoir (3), causing the fluid within to evacuate through the dispensing port (2), which may be part of a hub (9) attachment, or may be an integrated element within the body (1). A cap (7) can be included to cover and protect the injection end (e.g., the dispensing port) of the device.

Mechanical Considerations, Solutions, and Features

There are many combinations of mechanical pairings and procedural designs whose implementation may provide the desirable characteristics for one or more applications. For example, auto-injectors can enable rapid, accurate dosage of pharmaceuticals or other fluids. This technology is typically implemented either for simplicity and reliability by a healthcare practitioner, or for broad, rapid, standardized administration of allergy related anaphylactic therapy. The disclosed injection device can be used for medical or healthcare applications and can comprise materials that are biocompatible, medical grade, or have low levels of harmful extractable or leachable chemicals. The injection device can also comprise materials which are compatible with radiation, exhibiting minimal degradation or discoloration when exposed to a cumulative radiation dose of about 100 kGy or less. For example, the junction component or other components can be designed to be irradiated while the reservoir is filled with a polymer, hydrogel, drug compound, or biological compound and to later inject such a material having experienced cross-linking or other mechanical property alteration.

Certain product requirements may encourage additional focus on static—or steady-state—properties. For example, in the case of a device which is pre-filled with a substance for later administration, the device may also be looked at as a storage unit for the substance, necessitating consideration for stability of the stored substance. Such considerations may include material selection, substance composition, surface area exposure, and packaging, to name a few. These elements which allow the device to reliably store the pre-filled material are discussed in greater detail throughout this disclosure.

There are some applications where the simplicity and speed of an auto-injector are desirable, in addition to features which support precise and reliable delivery of materials with unique properties. In some cases, injection may need to target a specific region with specific access requirements. As previously described, the type of material being injected may also have specific requirements, where parameters such as injection rate and pressure tie in with material viscosity, or in the way that reactive materials need to attain a certain depth prior to undergoing a change of properties. The latter may also be observed in, e.g., the case of environmentally sensitive materials.

Such materials can respond to the specific stimuli, like temperature, pH, light, moisture, or other potential environmental differences upon exposure, which can alter their mechanical or chemical properties either reversibly or permanently. This dynamic behavior can result in significant changes to viscosity, stiffness, liquid retention, pharmaceutical ingredient retention, adhesion, and other properties which enable the material to be uniquely multifunctional. Thus, a need is present for an administration device which enables controlled application of a variety of materials with a variety of behaviors—pharmaceutical or otherwise chemically inert—with specificity, simplicity, rapidity, and reliability.

The mechanisms, features, assemblies, and functions provided herein are some of the ways in which desirable device behavior parameters and human factor optimization can be achieved. In one aspect, the elements described herein are useful in the construction of a device that can provide precise, rate-controlled delivery of a substance including, but not limited to, thermally responsive hydrogels, smart materials, polymer gels, polymers, elastomers, drug compounds, adhesives, drug eluting compounds and formulations, aqueous solutions and other liquid formulations, and biological compounds for the purpose of occluding biological vessels, delivering pharmaceutical or other kind of therapy, bonding elements, introducing an element for conduction of flow (electrical or otherwise).

The mechanisms, features, assemblies, and functions provided herein may be particularly useful for viscous materials, both Newtonian and non-Newtonian, having viscosities from about 500 cp to about 20,000 cp, or about 3000 cp to about 15000 cp, although this should not be construed as excluding the consideration of materials having lesser or greater viscosity from this disclosure.

Ergonomics and human factors can play a significant role in the usability and effectiveness of a device across a population of users; it is important and notable that the device can contain certain features to this end. In some aspects, the body can be small enough that it fits in the hand of users of most sizes, but large enough that it is not difficult to manipulate while wearing disposable gloves and with easily accessible features. In some aspects, the body is longer than it is wide, such that it may be held like a pen or like a wand. In some aspects, the body may have a section, widening along an arc, that provides a surface for gripping and which may include a feature, such as small, spaced extrusions, bumps, dents, or a soft, high friction material to serve as a gripping surface. In some aspects, such a section may capture the center of mass and serve to bias the center of mass towards the distal half of the device. In some aspects, the point of activation is accessible through a break in the continuity of the body and may occur on or near the center of mass. In some aspects, the method of activation is positioned such that it may be activated with the digits of hand that is holding the device and in a way that is comfortable to the user, such as with the thumb at the point where one would usually use the thumb to grip a pen, or the index finger at the point where it naturally lies on the construction described.

It may be useful for the design to include a feature which allows the user to adjust for the injection dose. In some aspects, this may comprise a rotary mechanism, such as a gear, which causes another component to travel distally or proximally such that one of those directions is associated with lowering the dose and the other in increasing the dose delivered. In some other aspects, it may involve a sliding component that serves as a limiter for other moving components. In some aspects, this may involve limiting the maximum travel distance of the plunger, thus creating an analog—or in some aspects, stepped—scale where the plunger is only able to drive the stopper into the fluid reservoir by a corresponding, limited distance, resulting in a pre-determined percentage of the maximum possible fluid delivery.

It may be useful for a single device to contain multiple reservoirs for injection. In some aspects, this may comprise one reservoir at each end of the device. In another aspect it may comprise one component containing multiple reservoirs which can be accessed much in the way a microscope switches between focal lenses. In yet another aspect, this may comprise a rotary-capable component which has several reservoirs that may be prefilled and expel the fluid upon sufficient rotation to fulfill some geometric condition, or which may receive fluid through the act of rotation, or some combination thereof. In some aspect these doses may be the same and in some they may be different, and in yet others, they may be different formulations or materials altogether.

In some aspects, a cartridge or replaceable component may contain the reservoir, allowing cycling between unused, pre-filled components. In some aspects this may include a stopper or plunger component as well. For example, a junction component (9) can be detachably attached to the body (1) as a replaceable component. FIGS. 11A-11F illustrate examples of junction components (9) comprising a threaded end that can allow the junction component (9) to be attached to or detached from the body (1) of the injection device. In some aspects, there may be cartridges available—having different volume injection sizes, with these volumes having been predetermined, for example, by a pre-set stopper depth—for attachment to a reusable primary device.

In some aspects, a cartridge is sealed by using the injection port cover and stopper, as described in this disclosure, with the stopper having been set to a pre-defined depth and in position to receive the plunger element at the time of assembly for use. In some aspects, the cartridge may additionally, or independently be sealed using a plastic and/or foil cover, heat sealed in place, for example, and which may either be removed to access the reservoir or which may be punctured by the device to grant direct access. The cartridge may also be packaged as discussed in this embodiment to reduce the potential for environmental influence on the properties of the substance and performance of the device.

The device, especially in reusable manifestations, may include an easily accessible feature for resetting the mechanism of actuation. In some aspects, this may include pushing, sliding, or pulling a plunger towards its initial position. In some aspects, the plunger is moved until the component responsible for creating a geometric constraint is able to return to its interlocking, inactivated position. In some aspects this may comprise winding a coil, compressing a spring, toggling a switch; or some action that represents returning the system to a firing-ready state.

In some aspects, injection efficiency is only a valued parameter with respect to cost saving, by reducing the amount of wasted fluid or material. Injection may not need to be optimized for efficiency, but rather, a more valued parameter is for the system to inject a specific range of volumes consistently. In some other aspects, injection efficiency is highly valued, as available dosage and injection volume should coincide when more complex user relationships, risks, and cost structures are involved. In cases where accurate injection may be more valued than efficiency, designs that eliminate variables and ensure consistency may be beneficial.

In some aspects, the design may include a paired geometric consideration, wherein the reservoir (3) and the stopper (4A) do not interfere until the stopper (4A) is as close to the filling point as possible, thus allowing venting and preventing the capture of air, which could cause leakage, fluid integrity issues, or injection inconsistencies. Examples are provided in FIGS. 11A and 11B.

In some aspects, a reservoir (3) may be designed to be filled with a larger quantity than the intended injection bolus. For example, the reservoir (3) may be filled with enough liquid that the device assembly can cause the stopper (4A) to enter the reservoir deeply enough (e.g., a defined distance) that some of the liquid or material is forced out the dispensing port (2), thus priming the injection system. The reservoir (3) can contain a volume after priming that is greater than the intended injection volume by, e.g., about 5% to about 2000% or about 10% to about 50%. The presence of internal pressure may additionally help to ensure that an airtight seal has been formed within the barrel (or inner surface) of the reservoir (3). In some aspects, the reservoir and stopper geometries may be designed such that the stopper (4A) forms a seal against the reservoir wall approximately at the top of the liquid fill level, thereby forcing encapsulated air out the back of the reservoir (3) so that very little air is trapped in contact with the fluid or material, which is beneficial for fluids or materials which may react with the air over time. Purging air from the system in this method, or by using a stopper designed to vent air during or after creating a seal, means that reservoir volume displacement translates directly to volume of fluid ejected, instead of compressing air, for example. Additionally, the use of a reservoir volume exceeding the intended injection volume enables the use of extended channels (11) and geometries. These channels, which can help bridge large changes of cross-sectional area, such as that present when comparing the barrel (3) and the injection port (2), can improve flow laminarity and injection precision. The above features may be observed in the geometric design of stopper (4A) and reservoir (3) in FIGS. 11A-11F.

Figure 11B:
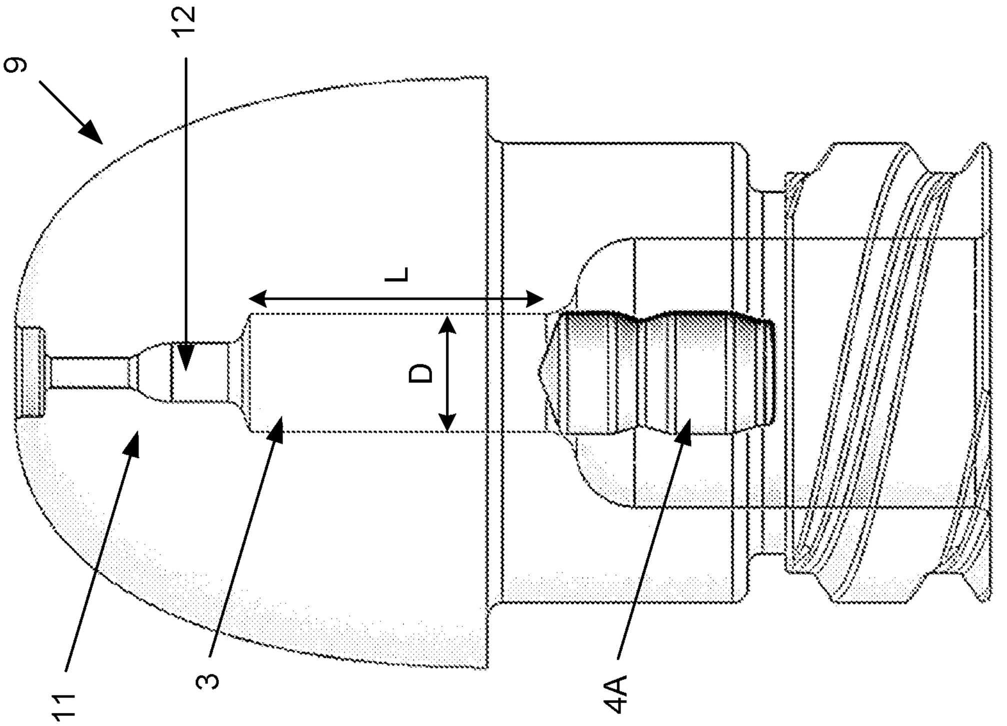
FIGS. 11A-11H illustrate examples of reservoir and stopper interference and plunger configuration relative to the stopper, in accordance with various embodiments of the present disclosure.
Figure 11A:
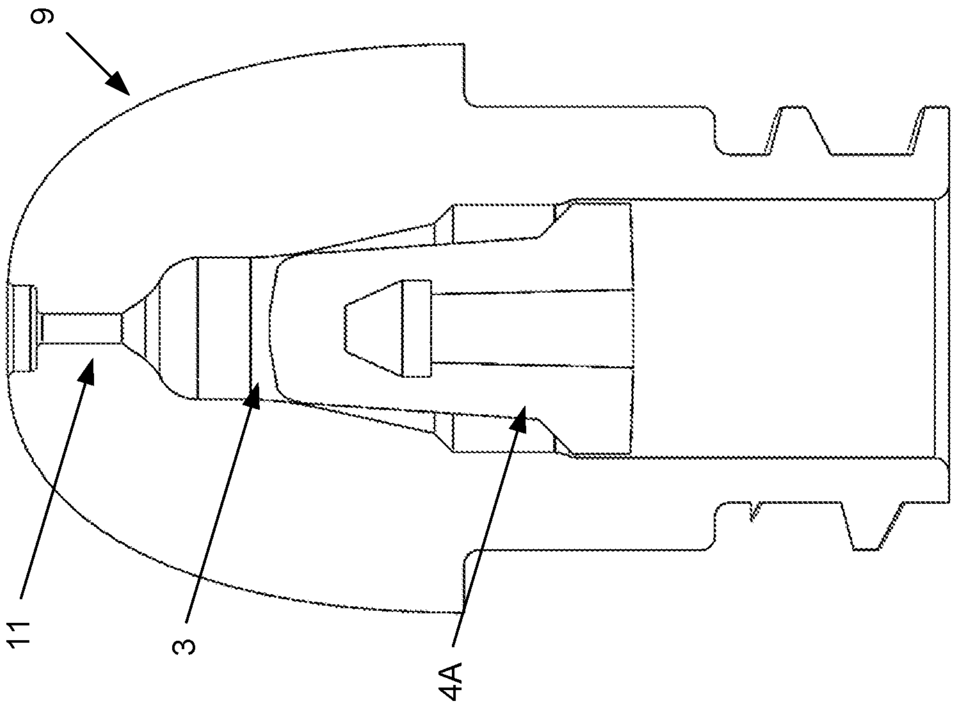
Figure 11C:
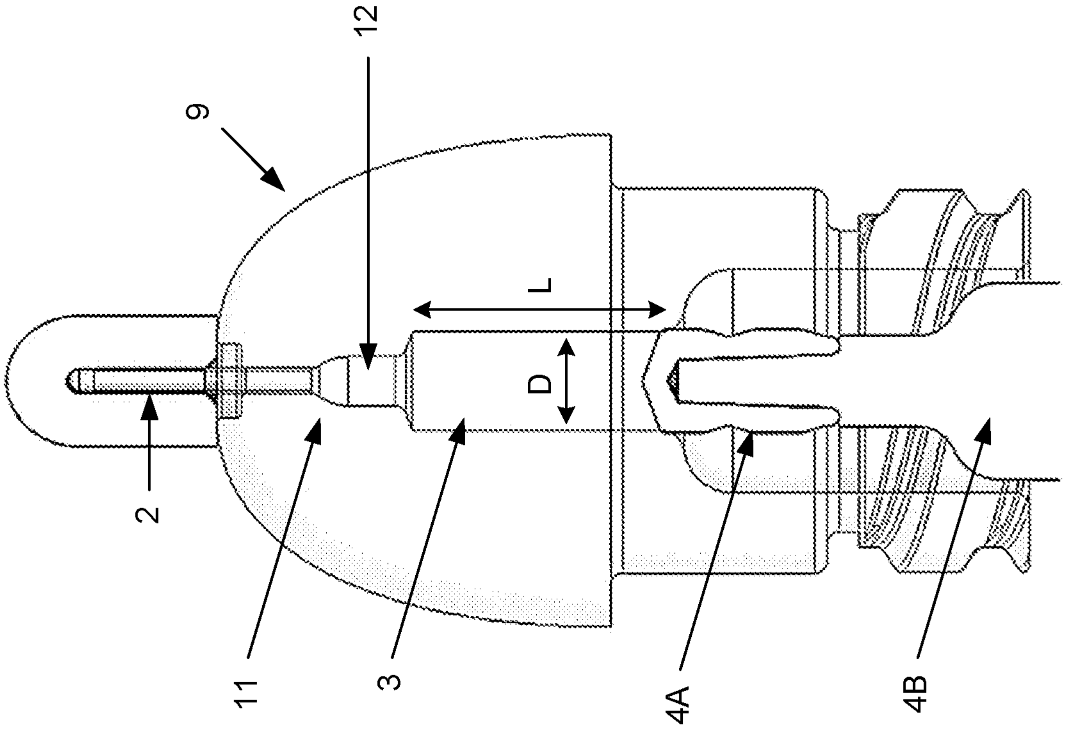
Figure 11D:
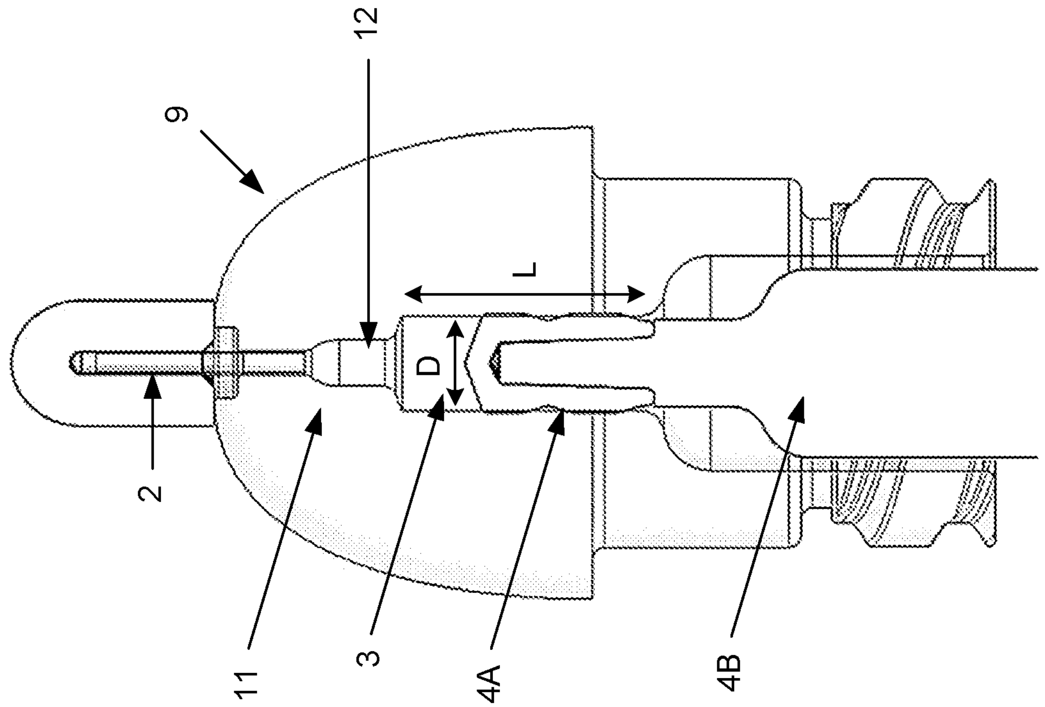

FIGS. 11A-11H illustrate examples representing some possible configurations of hub (9), stopper (4A), and plunger (4B) for purposes including, but not limited to those discussed in greater detail in the above paragraph and throughout this document. FIGS. 11A and 11B illustrate examples of a stopper (4A) and hub or junction component (9) arranged for the expulsion of air at the time of installation. The introduction of the stopper (4A) into the reservoir (3) can purge most or all of the air otherwise present in the reservoir (3). The reservoir geometry can enable the stopper (4A) to be introduced and create a seal while purging most of the air otherwise present, e.g., by establishing the fill level to approach or match the proximal cross-section of the initial interference of the reservoir (3). In some aspects, this air purging may also be achieved by the use of a stopper (4A) designed to vent through its body. These examples present one solution and should not be construed as excluding, for example, venting stoppers (4A) from the considerations of this disclosure. FIG. 11A also illustrates a dual expulsion and sealing interference fit, coordinated with the geometry of the reservoir (3). This element could additionally provide greater stability during translation.

FIGS. 11-11D illustrate one possible configuration of plunger and stopper mating, such that a cavity is present in the hub to receive the plunger and stopper. These figures also illustrate how the positioning of the plunger and stopper may be used to adjust the injected volume. The ratio of reservoir diameter (or width) D to total barrel length L or to primed length, as illustrated in FIG. 11B and FIG. 11 E, should be considered for filling and priming. This ratio can vary depending on, e.g., the volume of fluid or material to be stored in the reservoir (3) and other operating characteristics of the injection device. The additional reservoir length can assist in filing the reservoir (3) with the fluid or material in addition to sealing and venting air from the reservoir (3) during insertion of the stopper (4A). Additionally, this length can provide surface area needed for the stopper to create a seal against. It should be noted that the length of the stopper is a factor in establishment of stopper depth, as well, since there is a minimum depth required to create a seal. In one embodiment, among others, a hub is a prefilled element for use with a hand-held, rapid, auto-injecting device for delivering about 0.1 μL to about 20 μL (illustrated by example in FIG. 11D), wherein the total barrel length of the reservoir (3) can be about 1 mm to about 20 mm or about 3 mm to about 9 mm, the primed length can be about 0.1 mm to about 5 mm or about 2 mm to about 3 mm, and the diameter can be about 0.1 mm to about 5 mm or about 0.5 mm to about 3 mm. In other aspects, the ratio between D and L and between D and the primed length can both be from about 1:1000 to about 10:1.

Figure 11F:
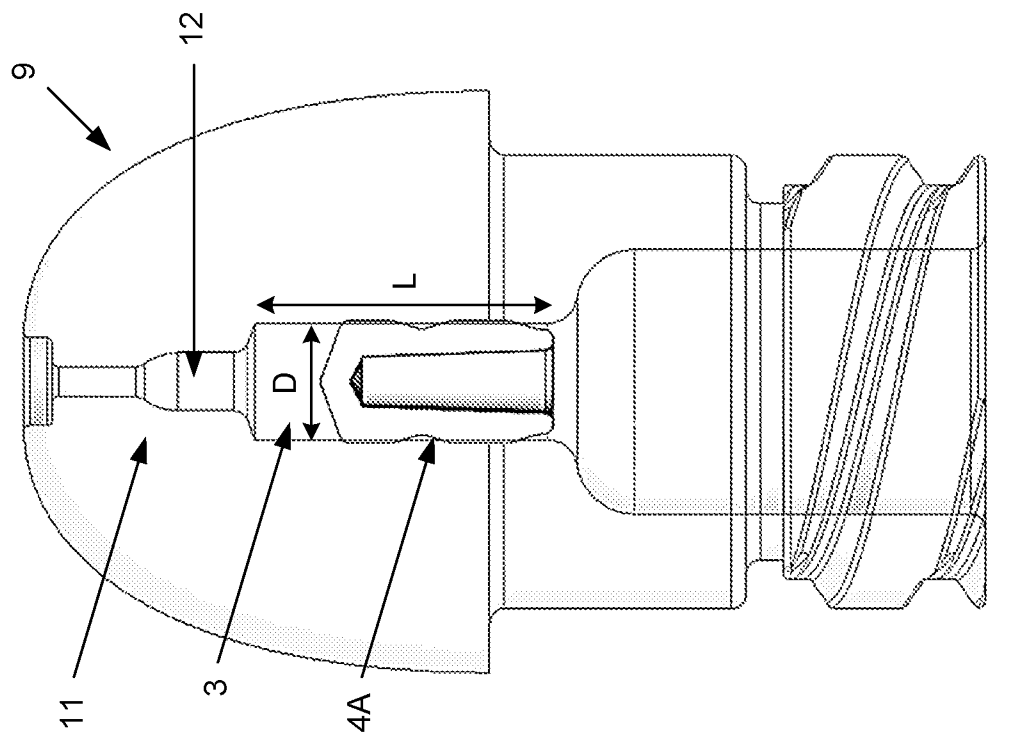
Figure 11E:
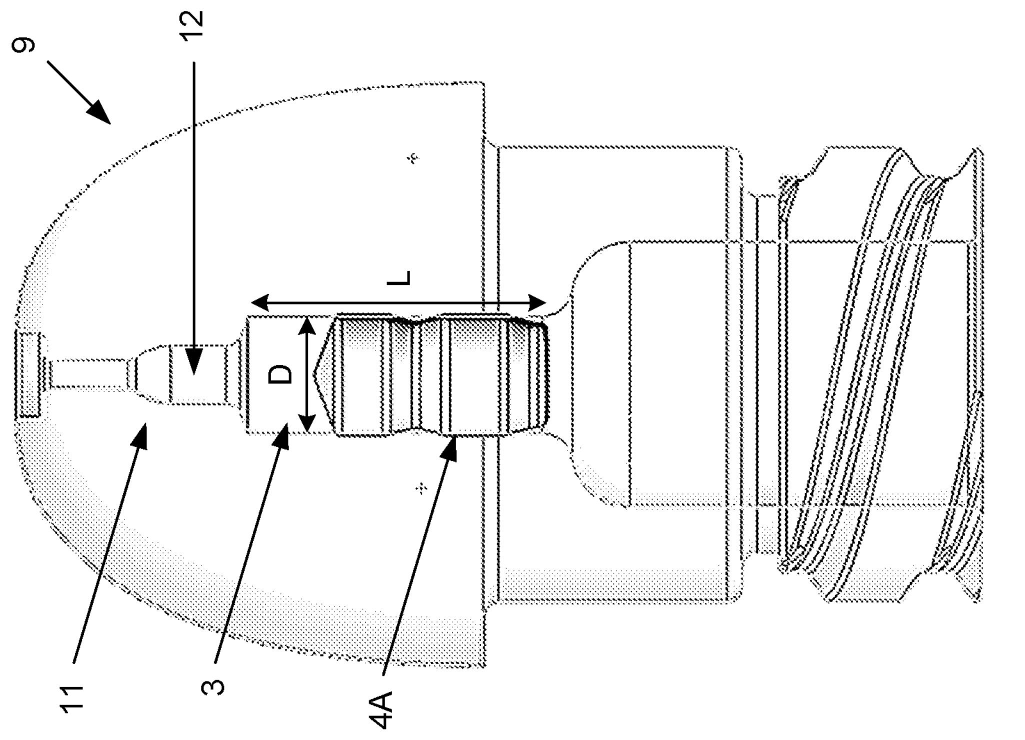

FIGS. 11E and 11F further illustrate an example of designs considered in this disclosure, such that the stopper (4A) creates interference with the reservoir barrel, such that the degree to which stopper diameter is greater than reservoir diameter can be in a range between, e.g., about 0.1% and about 25%, about 1% and about 15%, or about 3% and about 9% diameter. These illustrations may additionally draw attention to the use of ridges on the circumference of the external surface of the stopper (4A), in order to reduce contact surface area and friction, while providing stability and sealing assurance against leakage.

Figure 11H:
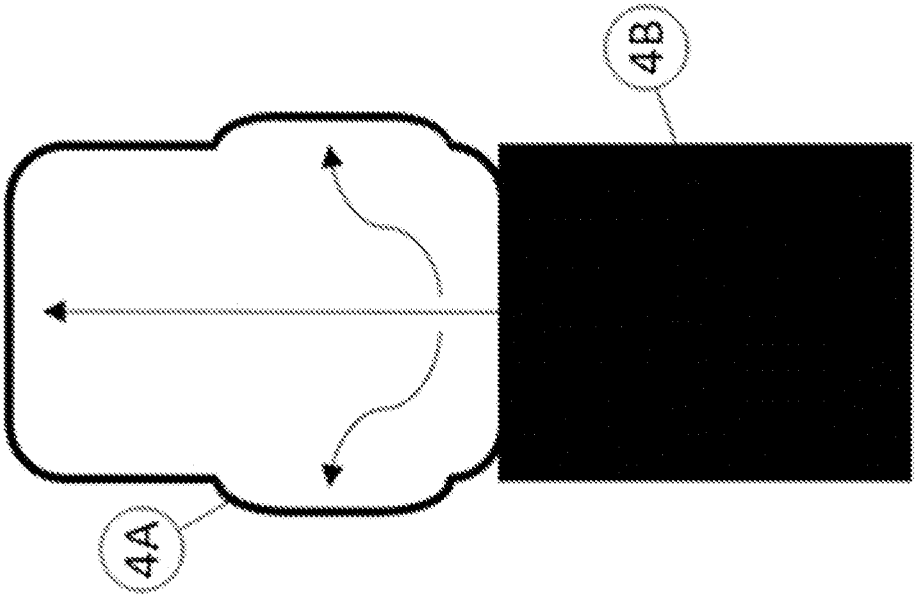
Figure 11G:
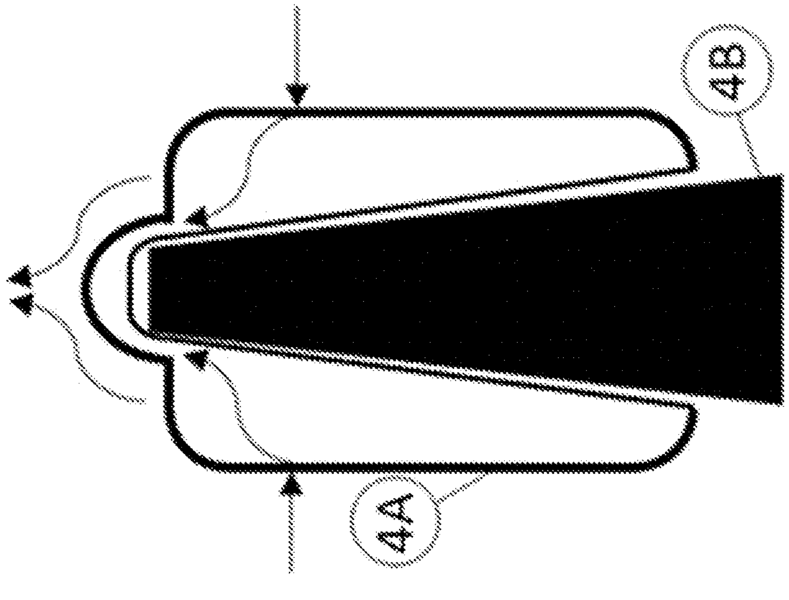

FIGS. 11G and 11H illustrate two examples of how configuration of stopper and plunger geometries may be used to influence the behavior of the stopper (4A) during injection.

These examples present only two possible configurations and should not be construed has precluding other geometries or mating configurations from the considerations of this disclosure.

In some aspects, the stopper and reservoir geometries may be designed such that the stopper, prior to activation, is only able to travel a pre-determined distance into the reservoir—associated with a corresponding, pre-determined resulting volume—before reaching a stop. In some aspects, the actuation mechanism may also be designed to reach a travel-limiter, such that the distance it causes the stopper (4A) to travel is pre-determined. For example, this may be a geometric constraint between the housing element and the actuation mechanism, but other appropriate limiting mechanism may be utilized depending on the method of actuation. In some aspects, the stopper (4A) may be designed to reduce transverse and/or radial movement, for example, by reducing the ratio of length to thickness from, for example, about 10:1 or higher, to for example, about 4:1 or lower, by increasing the stiffness of the stopper to a tensile modulus (at 100% strain) from, for example, 1 MPa to about 3 MPa, or up to about 10 MPa, depending on the degree if instability or undesired movement, and/or by introducing features to provide support, such as a rigid internal member or mating plunger (4B), as illustrated by the examples in 11C and 11D, or configuring the reservoir barrel to interfere with the stopper (4A) in multiple locations, as illustrated by the example in 11A.

In some aspects, the sensitivity of the volume relative to variation in the axial position due to component and assembly tolerance may be reduced by controlling the reservoir dimensions. It may prove beneficial to injection accuracy to decrease the reservoir width (or diameter when a cylindrical barrel is presumed, as below) while conserving the specified volume through a proportional increase of barrel length. The volume of a cylinder is given by $$V = \frac{\pi D^2}{4} L,$$

which illustrates that volume is proportional to the square of the diameter (D), but only linearly proportional to the length (L), therefore, for every unit increase to diameter, the total length needs to decrease by a greater quantity, so a larger fraction of total volume is captured within each unit of axial distance. This results in a higher sensitivity of volume relative to variation in axial position. Additionally, in a system-assembly of components, dimensional and mating tolerances need to be accounted for, including the effect of their cumulative offset from nominal positioning. Given that the diameter of a reservoir barrel is fixed, while the axial positioning of the stopper remains variable, the use of a smaller diameter in a volume-sensitive system may serve to reduce the total uncertainty and improve precision for injection volume per unit of axial distance travelled. This is particularly true for a system which relies on a specific pre-activation and post-activation positioning to determine the volume which may be dispensed.

The volume of fluid that is desirable for filling or for initial volume after filling, but prior to usage, and for injection may depend on the application, however some relationships between fill or initial volume, injection volume, and injection site may be useful for creating an optimal solution. In some aspects, the method described above, where the fill or initial volume is greater than the intended the injection volume may provide a benefit to injection consistency and accuracy.

In some aspects, the injection site may impart constraints on the injection parameters which may be used to the designer's advantage. For example, when reflecting on the scenario of injection into a channel which is sealed at the time of injection and which has varying internal volumes and desirable injection volumes, there may be merit to characterizing the channel's internal pressure resulting from injection. In some aspects, a smaller channel may produce a greater internal pressure, thereby counter-acting the pressure dispensing the fluid and reducing the total amount of fluid administered, compared to a larger channel. However, due to a difference in fluid contact surface area, it may be that the smaller channel requires less volume to be filled than the larger channel in order to be effective. In this case, it may be that a similarly desirable result is achieved in both cases. In this way, physical constraints that result in a natural self-regulation may be turned to the benefit of the designer.

It may be significant to the integrity of the bolus that external exposure is limited. In some aspects, the stopper (4A) may rest in a position that adequately seals the reservoir (3) against, for example, the entry of ambient air. In some aspects, this may also be solved through a cap—threaded or otherwise—or film secured to the openings, as would be suitable for refills or cartridges. In some aspects, the outlet may also be sealed from the external environment through the use of such elements or through the use of a tight-fitting, flexible cover.

Diffusion mitigation may be important to maintaining consistent solution composition within a pre-filled reservoir.

In some aspects, moisture content retention may be important to ensuring proper function of both the injector and the injected substance. If moisture transmission is not controlled sufficiently, the over-all range of effective use time and environmental conditions of the device could be compromised. Testing suggests that these may be particularly important when the volume of solution is very small and therefore is sensitive to even small amounts of moisture loss or gain caused by diffusion and/or evaporation over time or due to environmental conditions. By way of example, such low-volume cases may be considered to range from dispensed volumes of about 0.01 μL to about 1 mL, or about 0.1 μL to about 100 μL or about 0.5 μL to about 50 μL however such ranges should not be construed as excluding alternative definition of "low-volume" and further, should not be construed as precluding any disclosed elements from providing benefit to applications which make use of greater volumes. Control may be achieved through physical design, material selection, and environmental control/manipulation. In some aspects, ambient air diffusion may be important in preventing dehydration, oxidation, or other such effects. With respect to water loss, for example, the reservoir (3), stopper (4A), injection port cover (10), and/or packaging can be designed using low permeability materials (e.g., up to a maximum of about $1\times10^{-6}$ $cm^2/s$ by water diffusion coefficient and/or up to a maximum of about 10 $g/m^2$/day by moisture vapor transmission rate) and appropriate thicknesses to improve retention of substance properties over time. In other aspects, sensitivity of material properties to loss or ingress may also be reduced.

A variety of strategies for reducing sensitivity to moisture loss or other undesirable interactions may be employed to improve retention of substance or material properties over time, including, but not limited to use of increased volume of solution present in the reservoir (3) by about 10% to about 1000%, enhanced molecular bonding to resist reaction with external factors, among others. In some aspects, by understanding the viable range of solution concentrations, concentration at the time of manufacturing or processing may be selected based on the expected interactions; for example, a hydrogel which may experience dehydration may be produced at the lowest viable substrate concentration, so that the window of time during which dehydration may occur is maximized, up to the point where the highest viable concentration of solution is achieved due to moisture loss, assuming a water-permeable system. In some aspects, a strategic chain of processing operations may be employed to enhance the effective storage duration; for example, by hydrating a dry substrate at later chronological end-points, either by design, including but not limited to the use of some construction for hydration at the point of use, or by process, including, but not limited to dry substrate hydration at the time of device manufacturing.

In some embodiments, the sealed reservoir comprises a rigid barrel, a flexible pressurizing element and/or cartridge sealing element, an attached dispensing port, and a dispensing port cover. In some aspects, there are additional, secondary seals around any of these elements to enhance their effect as a barrier and—in some cases—mitigate the potential effects of a high moisture gradient between the reservoir and the environment. In some aspects, materials including, but not limited to cyclic olefin polymers and copolymers, cyclic olefin or metal compounded or layered materials, polypropylene, glass, and others which exhibit low permeability may be used to augment the reservoir element's ability to pose an effective barrier, especially for the reduction of moisture transmission. In some aspects, but not all, the above materials, in addition to materials including, but not limited to those such as fluorocarbons/fluoroelastomers, rubbers; butyl, EPDM, vulcanized (such as Santoprene) or otherwise, and combinations thereof; broadly including thermoplastic elastomers (TPEs) and thermoplastic vulcanizates (TPVs), and materials otherwise dipped, coated, layered, or loaded with any of the above material or additional materials exhibiting a similar property are considered for use in sealing elements (e.g., stopper and injection port cover), particularly with respect to capitalizing on the desirable properties of physical flexibility and degree of moisture impermeability.

The scope of selected materials is considered in regard to the specific requirements; for example, in some aspects, such as those where oil or gas permeability are of concern, materials such as EPDMs would be excluded as suboptimal candidates. In some aspects, surface treatment or coatings—hydrophobic or otherwise—may be applied to these materials or to those materials which on their own do not provide an adequate moisture barrier. In some aspects, the gauge of efficacy of a moisture barrier may be the diffusion coefficient, wherein a coefficient should be minimized. Testing and research suggest, in some aspects, a diffusion coefficient ranging from about 0 to about $1\times10^{-7}$ $cm^2/s$ may be considered to describe the degree of permeability which will allow for reliable moisture retention on the microliter scale for an extended period of several months or more, where a coefficient approaching zero would be ideal. Similarly, if Moisture Vapor Transmission Rate (or Water Vapor Transmission Rate) is used as the point of reference, a rate of 3.90 $g/m^2$/day may represent this indicator of upper range. It is understood by those skilled in the art that such figures and parameters are intended for example only and that the specific application and configuration of the embodiment will affect how beneficial properties and associated numeric values are evaluated; including, but not limited to, expected encountered temperature range; whereas elevated temperatures result in elevated levels of permeation and absorption, and the parameters indicating degree of prevention of specific undesirable interactions, such as those with gas or oil (e.g., gas permeability coefficients).

Design and total exposure area can also be significant. A small enough surface area with a higher degree of permeability may still be viable, with respect to the considerations described above. By Fick's law, diffusion is directly proportional surface area exposure and inversely proportional to thickness. Those skilled in the art will appreciate that these considerations and indicated selections reflect a possible solution for but one particular set of conditions, as described above, and the indicated design parameters should not be construed to suggest that no other ranges of materials or ranges of quantitative properties are imagined within the scope of this disclosure. In some embodiments, wherein the level of sensitivity to such considerations is lower, the allowable level of permeability may be great, while conversely, in the case of higher sensitivity, there may yet be even tighter constraints than those levels outlined above.

It would be considered useful for there to be one or more features for imparting environmental control to the device and fluid. In some aspects, this control would present as thermal, conductive, magnetic, moisture, or some other form of insulation. In the case of a thermally responsive hydrogel, for example, insulation would prevent the fluid from responding prematurely. In some aspects, controls against variable humidity may also be desirable; wherein dry environments may expedite desiccation, humid environments may alter or degrade the device or solution function, or where a specific range of humidity presents optimal storage conditions. In some aspects protection against environmental effects may be achieved through selective impermeability, affected by the separating material and its thickness in the normal plane between the sensitive components and the environment. By selecting a material with a known water permeability, for example, and a desired water transmission over time, Fick's Law may be used to estimate the thickness required to achieve the desired degree of moisture retention. In some aspects, this protective effect may be achieved through the use of containing units, primary to the device, or secondary, as packaging. Such elements may include a barrier of metal, plastics or metalized plastics, such as a combination of layered polyester and aluminum. For example, the injection device can be packaged in a container comprising such materials, which exhibit low water permeability.

In accordance with Fick's law, wherein the rate of diffusion is directly proportional to the gradient of concentration of moisture (or conceivably, other substances), additional control may be granted through the use of a moistened fabric, or other unit or compartment capable of storing and releasing moisture in order to maintain relative humidity within the enclosed environment. Conversely, in yet some other aspects, but not all, some feature that passively desiccates the fluid would be useful for maintaining the desired moisture level in, for example, water-absorbing gelling materials. In some aspects this may manifest as a cavity within the wall of the reservoir where air or some other insulating element, such as a polyurethane foam may be contained. In some aspects, this concept is further expanded by disclosing features for active control; such as active cooling of a thermally responsive hydrogel, for example, by means of initiating an endothermic reaction, or active heating by means of an exothermic reaction. The junction component (9) can include an activatable heating or cooling element to enable conditioning of a thermally responsive material prior to injection.

In some aspects, user selected active cooling may involve a cavity or chamber within the wall of the hub, for example, that contains a barrier between two compartments containing and which have a mechanism available to the user for removing or breaking down that barrier, thus allowing the mixture and reaction of these components in order to draw heat from the surrounding area and ensure that a thermally responsive hydrogel, for example, remains in a flowable state at the time of injection. The contents of the chambers can comprise, e.g., water and ammonium nitrate, or other combinations present in common commercial products which produce and endothermic reactions.

In some aspects, user selected active heating may involve a resistor within the hub or junction component (9) which may be used to generate heat when connected to a battery. In some aspect, a cavity or chamber within the wall of the hub, for example, can contain a barrier between two compartments containing and which have a mechanism available to the user for removing or breaking down that barrier, thus allowing the mixture and reaction of these components in order to release heat into the surrounding area and warm a bolus at the time of injection. The contents of the chambers can comprise, e.g., water and calcium oxide, magnesium sulfate, or other combinations present in common commercial products which produce and exothermic reactions.

In some aspects, the reservoir can contain a barrier between two compartments containing substances that can be combined prior to injection. The barrier which may be removed to allow the combination of multiple substances. The substances can be combined to form a shape adaptable material. For example, the substances can comprise a polymer and water, which create a hydrogel after combination.

A more natural transition between reservoir (3) and injection site may prevent stagnation, backflow, and may reduce level of inertial forces, resulting in smoother fluid flow. Thus, in some aspects, the geometry of the reservoir (3) can be optimized for minimal interruption to fluid path. In some aspects, this may involve contouring and removal of sharp angles and/or a gradual transition from a larger to a smaller diameter channel. In some aspects, the desired capacity of the reservoir is achieved by using a minimized cross-sectional area and a longer channel height, as opposed to a short, wide reservoir. This concept is also illustrated in FIGS. 11A-11F; however, this should only be considered as example and not as the only design conceived of regarding geometric transitions.

FIGS. 11B-11F also illustrate an example of the configuration of the dispensing channel (11) between the reservoir (3) and the dispensing port (2). As shown, the dispensing channel (11) can comprise a plurality of reduced diameters or widths to facilitate the controlled supply of the fluid or material from the reservoir (3) out of the dispensing port (2). The dispensing channel can comprise one or more intermediate chambers or sections (12) with different barrel diameters or widths to reduce or minimize turbulence of the fluid or material as it is forced from the reservoir (3) by the stopper (4A). A first intermediate chamber or section (12) at the distal end of the reservoir (3) can have a barrel diameter that is about 25% to about 95%, or about 45% to about 75%, of the barrel diameter of the reservoir (3). The transition between the reservoir (3) and the first intermediate chamber (12) can have a curvature of radius of about 20% to about 100% of the barrel diameter of the first intermediate chamber (12). This can improve injection consistency and material integrity. Subsequent intermediate chambers can have a barrel diameter that is about 25% to about 95%, or about 45% to about 75%, of the barrel diameter of the preceding intermediate chamber. The transition between the preceding intermediate chamber and the subsequent intermediate chamber can have a curvature of radius of about 20% to about 100% of the barrel diameter of the subsequent intermediate chamber.

In the example of FIGS. 11B-11F, the end of the reservoir (3) smoothly transitions to an intermediate chamber (12) having a diameter smaller than the reservoir barrel to reduce turbulence of the fluid or material as it is ejected from the reservoir (3) by the force applied through the stopper (4A) and plunger (4B). The intermediate chamber (12) smoothly transitions to a portion of the dispensing channel (11) that directs the fluid or material to the dispensing port (2). As this point, the dispensing channel has a diameter that is substantially the same as the dispensing port (2). The smooth or tapered transitions can reduce turbulence in and resistance to the flow of the injected fluid or material. In the example of FIGS. 11B-11F, the length of the intermediate chamber (12) can be about half (e.g., about 2 mm) of the total dispensing channel length (e.g., about 4 mm) from the reservoir (3) to the inlet of the dispensing port (2).

In some aspects, the stopper (4A) is constructed in a form and from a material that imparts pliability, while remaining stiff enough to translate with little or no transverse strain when pushed across a relatively large surface area.

In some aspects, the stopper (4A) can be made from a lubricious material that serves to reduce sliding friction. Further, the thickness of the interfacing geometry may be non-uniform in order to reduce the amount of surface area in contact with the surrounding wall, or selectively thicker in order to create a greater amount of friction, if desirable. In some aspects, this non-uniform thickness may allow a greater degree of transverse deformation when the stopper is compressed axially, which may provide a more effective, dynamic seal against the reservoir wall when injection reaches the end of its stroke, which may provide additional protection against back-flow.

In some aspects, the geometry will create a seal with the reservoir at its distal end, while the proximal end serves to stabilize and ensure straight translation, which may or may not involve a seal against the containing wall.

In some aspects the stopper may have a thinning neck between the proximal base and the distal head, where the seal is created. In some embodiments, the distal head and/or proximal base can include ridges encircling the stopper (4A) as illustrated in FIGS. 11B and 11E. In other aspects, it may have a gradual transition from thicker body to thinner head. In yet other aspects, the stopper (4A) may have a uniform thickness. In some aspects, the distal head may terminate in a distally extending curve or angle.

In some aspects, the stopper (4A) may be decoupled and unconnected to a plunger (4E) or affecting component, while in some other aspects they may be mated by some internal feature, such as a complementary cavity or threading, as illustrated by the example of a stopper cavity in FIG. 11A. In some aspects, the stopper (4A) may have an internal cavity that better allows the plunger (4E) or effecting component a larger interface area and which may allow such a component to cause distal expansion of the head into the distal end of the reservoir at the end of the injection stroke to artificially increase the volume theoretical displacement.

The plunger length and/or distal geometry (e.g., prong) can be used to set the depth of the stopper (4A) based on the distance traveled between an initial set depth and an end-position of translation, corresponding to the desired volume. The injection volume can range from about 0.1 μL to about 250 μL, or about 0.1 μL to about 200 μL, or about 1 μL to about 100 μL, or about 1 μL to about 50 μL, or about 1 μL to about 25 μL, or about 1 μL to about 10 μL, or about 2 μL to about 5 μL. For example, for a barrel similar to the example given by FIGS. 11B-11F, a depth of about 1 mm to about 5 mm can correspond to a delivered volume of about 1 μL to about 16 μL. The injected volume can be manipulated freely depending on the length of the stopper (4A), plunger (4B), or a combination of the two, resulting in a delivered volume of about 1 μL to about 16 μL. The stopper (4A) may be set to any number of distances as it moves from the proximal end-position of the reservoir (towards a distal end) with a travel distance up to a stop distance of about $9/10^{th}$ of the total length (or depth) of the reservoir barrel or less, depending on the sealing capability and requirements of the stopper.

In some aspects, the specific construction, configuration, and mating of the stopper (4A) and plunger (4B) may be designed to provide a particular desirable behavior. For instance, the relative position, geometries, and stiffnesses of such components may be used to selectively time and transmit the application of force and cause movement, and/or deformation. In some aspects, the utility of such behavior could arise, by way of nonexclusive example, as illustrated by FIG. 11G, from the interaction between a plunger (4B) with a mating protrusion for which the length is greater than the depth of the mating cavity of the softer stopper element; wherein the result of application of force is a deformation beginning as a protrusion along the central axis and further resulting in the radial contraction of the stopper (which may be described, in part, by the Poisson's ratio of a given material) and wherein such an interference-reducing behavior may impart benefits including, but not limited to, a reduced 'break-loose' and or 'glide' force (described broadly as the forces required to begin and sustain translation through a barrel) relative to the degree of static interference. Therefore, such a configuration may present an opportunity to produce an improved static seal, for purposes including, but not limited to storage and handling, while retaining desirable performance behavior.

In some aspects, the described configuration will impart a different behavior, for example, if the central contact point is less deep inside the stopper, resulting in a greater longitudinal thickness and an initial contact position closer to the surface most proximal to the force applying element, then the level of distal protrusion may be reduced and overcome by a higher degree of radial expansion, as illustrated by FIG. 11H. The exemplary case of such a scenario resembling contact between two flat faces of the two components with no cavity or mating protrusion from the plunge. In such a case, the radial expansion may generate a different effect of utility, for benefits including, but not limited to preventing leakage during injection by increasing the level of dynamic interference between the stopper and barrel. Those skilled in the art will, however, recognize that the interaction is dependent on a variety of variables such as the material stiffness, the rate of force applied, the degree of interference, the external surface geometry and radial cross-section, and the specific mating geometries, to name some, but not all considerations.

In some aspects, the behavior described is also heavily influenced by the materials selected. Material properties such as stiffness, hardness, lubricity, and toughness will affect the ability of a stopper (4A) to create a seal and determine how it responds to various rates of applied force. In the context of a rapidly actuated injection system which considers the above potential component configurations, a low stiffness and hardness may result in a greater degree of deformation relative to the transmission of force into movement. In other words, the stopper (4B) will expand or protrude to a greater degree when the material is less stiff and hard, within the same amount of time. A low stiffness material—wherein, for example, a modulus of about 1.5 MPa or below could be considered low stiffness—deforms more easily, meaning that the friction force resisting is likely to be lower than a higher stiffness material, given the same contact area and coefficient of friction, however the higher degree of deformation exhibited by lower stiffness materials may also result in greater contact surface area and/or compressive loading, depending on geometric constraints. Therefore, a balance needs to be struck between component geometries as well as material properties in order to elicit desirable performance; often indicated by consistent, low break loose and glide forces and absence of backflow or leakage.

In some aspects, the above consideration for stopper (4A) and plunger (4B) interaction may further be affected by the rate and mode of force transmission. When considering that the length of the prong relative to the length of the complementary cavity, extension of a spring (6) can introduce, for example, an impulse force through the plunger (4B) which, if the rear of the stopper (4A) is contacted first (e.g., prong length is less than cavity length), can cause the stopper (4A) to expand radially, increasing the interference fit with the reservoir (3) from a range of about 1% to about 10% to a range of about 2% to about 20%, thereby improving dynamic sealing and slowing translation. If the cavity allows distal protrusion of the stopper (4A) (e.g., prong length greater than cavity length), then it can contract radially, thereby reducing an otherwise high degree of interference from a range of about 4% to about 20% to a range of about 2% to about 10%, which enables improved static sealing, while reducing dynamic friction force. There may also be some permutation wherein, for example, contact is first made with the rear of the stopper, then upon axial compression of the proximal end of the stopper, the prong makes contact with the distal face of the cavity and causes radial contraction at the distal end of the stopper, for some additional result.

To provide an effective static and dynamic seal, the stopper material should be flexible enough to adapt itself completely to the contours of the interfering barrel. In some aspects, the a lubricious material is in itself not enough to guarantee proper performance; in the case of rapid injection actuation for instance, a low hardness material may perform more poorly than another material with higher hardness and low inherent lubricity, due to the effects described above. In some aspects, given an initiating spring force of approximately 21bf, a rapid force transmission is best served by a material with a shore hardness rating in a range of about OA to about 90A, or about 40A to about 85A, or about 30A to about 75A, or about 55A to about 75A (or the equivalent in other rating systems) and a tensile modulus (at 100% strain) in a range of about 0.1 MPa to about 100 MPa, or about 0.5 MPa to about 20 MPa, or about 1 MPa to about 10 MPa, or about 1 MPa to about 5 MPa, or about 2 MPa to about 4 MPa. It will be understood by those skilled in the art that the specified ranges describe one possible embodiment and does not exclude the consideration of other configurations from the disclosure. For example, these ranges may be shifted noticeably depending on the force applied, the rate at which force is applied, and the coefficient of friction of the material, to name several factors.

In many manifestations of the device, one can expect the presence of a rigid member which is acted upon to pressurize the fluid reservoir. In some aspects, this component is directly incorporated into the mechanism of activation, such that, for example, the member is under constant force from a spring (6) in compression, but remains static due to geometric constraints and which, upon release from those constraints, becomes free to move within the intended range of motion. In some aspects, this component can include a feature (e.g., prong) for mating or otherwise interacting with a stopper (4A) and a feature for mating or otherwise supporting interaction with an actuating component, such as a groove for constraining the end-face of a spring. In some aspects, this component is not subject to any external forces until the time of activation, which may be rapid and continuous—as in the case of a spring—or subjective to the external forces applied by the user—as in the case of manual injection.

The method of activation can be important when considering both the reliability of activation and the usability. The method should be simple and offer little resistance to the intended activation, but protect the device from faulty activation. The button can be colored differently from the body to provide visual distinction. In some aspects, this may be achieved through the use of a button which is roughly flush with the surface of the device when undepressed (e.g., to prevent accidental depression), sized about 9 mm or less to about 20 mm wide or more, and which can activate the device with a depression of about 3 mm to about 10 mm with a force of about 2.8N to about 11N. In some aspects, this may be achieved through selection of a spring—perhaps conical in nature—which provides resistance to depression relative to its constant and distance of compression. In some aspects, the activation can be achieved due to geometric constraints between, for example, a button and a plunger, wherein the plunger passes through a segment of the button which has openings shaped differently at different depths and wherein the two have interlocking geometries at the least depth and complementary, non-contacting geometries at the greatest depth. These depths may correspond to a specific plunger (4B) position which determines the depth of the stopper (4A) inside the reservoir, where upon release of the mechanism at activation, this position determines injected volume. In some aspects, this activation mechanism may be repeated using multiple depth ranges and a series of interlocking and complementary geometries along the axis of movement, much like a lock and key tumbler system. Such a feature would allow for a measured amount of activation to occur at each distinct depth. In some aspects, this feature may conform to other mechanisms of activation, such as the deformation of a constraining geometry. The description above should not be construed to preclude other methods for activation, including those suited to the means described in this document.

A locking mechanism provides a useful means for preventing unintentional or partial activation of the device. In some aspects, this may be achieved by a component providing geometric constraint against movement of the activating component until it is repositioned; as in the case of a switch.

One would expect that for rapid injection, a useful range of velocity would span from about 0.025 m/s to about 300 m/s. A useful range of velocity for non-rapid injection, intended to, for example, help control delivery of non-Newtonian fluids or reduce flow rate in a sensitive application, would span from about 0.25 mm/s to about 0.025 m/s.

In some aspects, but not all, the distance which must be travelled by the stopper to complete an injection is much less than the compressed length of a spring (6) providing an actuating force, where this ratio may be about 1:100 or less, or 1:25 or less, or 1:10 or less.

In some aspects, the compression spring (6) is not in constant contact with the plunger or stopper and may only transmit force after extending a certain distance.

When using a spring (6), the velocity of injection may be characterized by the mass of the component under force, such as a plunger, the spring constant (k) and the deflection; both components of the force generated by the spring. The acceleration of the spring is equal to the force divided by the mass of interest. The velocity of the spring when acting upon another component in the line of firing, such as a stopper, is given as of $v_f^2=v_i^2+2ad$, where the initial velocity is given by $$\sqrt{\frac{2\left(\frac{1}{2}kx\right)}{m}}$$

and d is the distance the spring unloads before reaching the next resistant object. Under the assumption that the subsequent object offers constant resistance, then $v_f$ of the mass in motion may be considered the variable that imparts control to injection speed.

In some aspects, a compression spring configuration may be designed to meet the desired injection rate. For example, a powerful spring (powerful, as defined by the spring rate (k)

and the extent to which it may be compressed in the considered application) relative to the known force required to complete an injection) can be compressed to a fully loaded length of about 10% to about 80%, or about 20% to about 50% of the free or resting length ($L_F$) to maximize the potential energy available (up to k(0.8 $L_F$)). In one aspect of this example, the spring force is not transmitted to the stopper (4A) until the spring extension reaches about 50% to about 100% or about 80% to about 95% of the free length, thereby imparting a force of about 0.5 $kL_F$ or less or about 0.2 $kL_F$ or less as an impulse when the spring's speed is near its zenith, having accelerated from its maximally compressed state. In some aspects, this impulse may additionally impact the rear of the stopper and cause radial expansion, resulting in greater friction and resistance to translation, further reducing the speed of injection.

In another aspect, a spring (6) can be compressed by about 50% or less, about 30% or less, or about 20% or less of its free or resting length ($L_F$). The spring may be selected such that injection force ($F_I$) at about 30% compression or less or at about 10% compression or less is larger than a known maximum resistance force experienced during injection (e.g., the resistance impeding axial movement of the stopper within the reservoir), thereby minimizing the spring's opportunity to accelerate while maintaining a high enough force to complete the injection. Thus, the injection force can be given by $k(0.3\ L_F)>F_i$ or $k(0.1\ L_F)>F_i$, for example, where k is the spring rate and the resulting rate of extension is proportional to this decrease in potential energy. The spring (6) described above can provide sufficient injection force at a controlled velocity, which may be slow enough to be particularly effective for automatic injection of non-Newtonian or other materials, including low viscosity materials (e.g., <1000 cp) which may benefit from a lower Reynolds number and improved resistance to turbulent flow.

For low-volume applications—including, but not limited to, dispensed volumes of about 0.01 μL to about 1 mL, or about 0.1 μL to about 100 μL or about 0.5 μL to about 50 μL—this disclosure provides examples of some of the considered solutions which present capability for flow rates of about 0.01 μL/second to about 1 mL/second, or about 0.1 μL/second to about 100 μL/second, or about 1 μL/second to about 25 μL/second. In one example, wherein the device is proposed for administration of a shape adaptable, temperature responsive material for the treatment of symptoms associated with dry eye disease, a flow rate of about 0.2 μL/s to about 50 μL/s or about 1 μL/s to about 10 μL/s is seen as desirable; however, such a range should not be construed as excluding other possible flow rates from the scope of what is considered by this disclosure. Further, the above ranges provide examples of some considered average flow rates and should not be construed as precluding variable flow rate from considerations herein, as would be seen in the case in some examples featuring an injection actuated by spring. This disclosure discusses the design considerations which can allow for control of flow rate, including, but not limited to, injection port diameter, reservoir size, force applied, rate of force applied, and material properties, such as viscosity.

In some aspects, the injection device can be configured to deliver about 90% or more of the injection volume within a defined time period, e.g., about 5 seconds or less by depression of a button to activate injection.

For non-Newtonian fluids, injection speed may be reduced to a level proportional to the rate of change in viscosity. The useful range of velocities vary with the individual characteristics of the fluid, but in some aspects, one can include velocities ranging from about 0.1 mm/s to about 0.5 m/s.

One important objective in adjusting injection is to ensure laminar flow. The onset of turbulent flow is yet another source of injection variability and reduction to injection quality or fluid integrity. The common tool for judging this quality—the Reynolds number $$\left(Re = \frac{uD\rho}{\mu}\right)-$$

considers the relationship between inertial forces and viscous forces. In the case of non-newtonian fluids, viscous forces are difficult to characterize because they are inconstant across the pressurized cross-sectional areas. One technique for addressing the quality of flow is to ensure that laminar flow prevails at the specific locations and moments in time where mean velocity and channel diameter (D) are highest, and where viscosity is lowest. The velocity profile and the viscosity profile are considered able to be derived from the no-slip boundary condition. The velocity is directly related to shear rate, an important parameter in the variability of viscosity, thus velocity and viscosity are paired, depending on the unique properties of individual fluids. It may be assumed that the impact of velocity is greater than the impact of viscosity along the profile, because the ability of the fluid to absorb additional energy cannot exceed the change of input energy, due to the law of conservation of energy. Additionally, the theoretical velocity at the boundary layer is 0 m/s, while the viscosity remains at a non-zero minimum equivalent to the fluid at-rest. Therefore, it may be assumed that the worst case for achieving laminar flow occurs at the center of the channel, where velocity is highest. The assumption is made that velocity of fluid precisely at the interface between fluid and stopper component is equal to the velocity of the stopper component itself. Thus, as velocity and cross-sectional area are conventionally proportional, the appropriate time and place for evaluating a system for laminar flow is at the point where the diameter is largest and when the component being actuated achieves its maximum velocity. By further assuming that the viscous and frictional resistances of the system are negligible, an overestimate of the Reynolds number can be achieved, which provides a basis for predicting which values assigned to each parameter will prevent turbulent flow. Such considerations are of greater importance for Newtonian fluids of low viscosity, but merit consideration in other cases nonetheless.

There are, however, a variety of tools for regulation of velocity along a given axis. In some aspects, this may resemble a worm gear and its mate, which require that the object acted upon by the spring follow a radially threaded pathway, such that the time to travel a given distance is increased in proportion to the number and pitch of threads. In some aspects this scaled automatic injection velocity may be achieved through the use of a torsional spring, which causes rotation to some worm gear, whose rotation causes the linear travel of a third component. In some aspects, the use of a resisting force, such as friction or transverse compression, may also serve to slow the movement of pressurizing components. In some aspects, a stopper with a diameter that is larger than its containing barrel may be used, such that the material type and the degree of interference determines the level of resistance to movement in the axis normal to its cross-section.

Control over injection speed is of particular interest in the use of responsive and multiphase materials, and/or materials which exhibit non-Newtonian behavior; for example, shear thickening. As example, when injecting a thermally responsive polymer hydrogel into the tear duct, a balance needs to be struck such that the fluid is able to attain the desired depth before the ambient body heat causes a transition to its solid state. If the injection is too slow, the reaction will occur before the fluid has traveled to sufficient depth. If the injection is too fast, the fluid will become more resistant to injection, subverting the intended dynamics of the procedure.

The injection of a bolus, particularly those with high viscosity (e.g., >2000 cp), which require greater injection force, may benefit from the use of pneumatic actuation enabling constant pressure and force. In some aspects, this mechanism may make use of a compressed air cartridge and a regulator, wherein a valve on the cartridge is opened, causing air to escape at a rate controlled by a regulator, such that the cavity entered by the air is pressurized and remains at the same pressure despite movement of plunger or other components because the regulator releases more air to compensate, so that the internal pressure of that cavity remains constant. In some other aspects, but not all, this pressurization may be achieved by manipulation of some component used to reduce the volume within the cavity at a rate corresponding to the volume gained by the movement of a plunger component. In some other aspects, a spring system that imparts a constant force may also aid in efficient injection.

In some aspects, the injection port can comprise a tube that extends from the junction component or hub. The injection port tube can be blunt-tipped or sharp tipped and can be made from a variety of materials including, but not limited to polycarbonate, PEEK, polyimide, stainless steel, PEBAX, PTFE, and PET. The injection port may also be considered to be any attachment which may transmit the injected substance from the reservoir to the site of interest. In this way, the injection port can be a disposable component, such as a needle or catheter for delivering a substance subcutaneously, or to an anatomical site for common medical procedures, for example.

The hub may feature either custom or standardized connectors, such as a luer fitting, to facilitate use of the injection device with consumable materials, including but not limited to needles, catheters, and reservoir cartridges. The device may be modular such that the reservoir may be connected to one or both of the body and actuation system and the injection port.

In some aspects, a shape adaptable material can be thermally responsive and be flowable at room temperature or below, or about 25° C. or below, or about 32° C. or below and can change properties when warmed past this threshold by the heat of a body. The junction component or hub (9) can be configured to prevent the user's body heat from causing transition prior to complete delivery to the target location. The injection device can be configured to facilitate rapid injection of the shape adaptable material into a subject and delivered to the target location prior to their body heat causing its transition. The shape adaptable material can be a responsive material which is sensitive to environmental factors and the injection device can be configured to insulate the material from the conditions which would alter its properties.

All mechanical modalities described above should be considered to have been conceived of in all possible combinations and permutations, which may solve for the desirable characteristics described herein. Further, mechanisms, assemblies, and functional components of common knowledge to those skilled in the art should also be considered to have been conceived of among these possible permutations and combinations.

Applications and Materials

The embodiment discussed above is a generalized form of common intracutaneous injection devices and intends to expand the scope of viable applications while also contemplating the unique properties of materials used in conjunction with the device, such as hydrating or thermally responsive materials, but not exclusively such substances. Examples of some applications and materials of interest are provided below.

Punctal Plug for the Treatment of Dry Eye

Background of Dry Eye Application

One preferred pairing of material and application may be derived from, e.g., U.S. Patent App. Publication No. 2018/0360743, which is hereby incorporated by reference in its entirety and is primarily interested in the use of thermoresponsive hydrogel as an occlusive agent for treating the symptoms often associated with dry eye syndrome (otherwise known as dry eye disease). The spirit of this disclosure expresses a viable solution for other materials and for all viable materials at a variety of anatomical locations.

Dry eye syndrome occurs when there is insufficient protection of the eyes by the film of tears that typically cover them. Those with dry eyes often report difficulty with activities such as reading, computer use, watching television, and driving. Current solutions are subject to a host of complaints, which may be resolved with the disclosed devices.

The current technologies used for the treatment of dry eye syndrome include: over-the-counter (OTC) eye drops, pharmaceutical eye drops, hard, pre-molded plugs, and plugs which are inserted and hydrate in-situ. Plugs are generally installed using forceps and/or a simple insertion tool, which for example, presents the plug at the tip and then retracts a retaining element. These plugs are further divided by material and by occlusion site (punctal vs. canalicular), but the focus of this section is to show how the current modalities, in their shared, general form, exhibit characteristics which are generally problematic.

Figure 12:
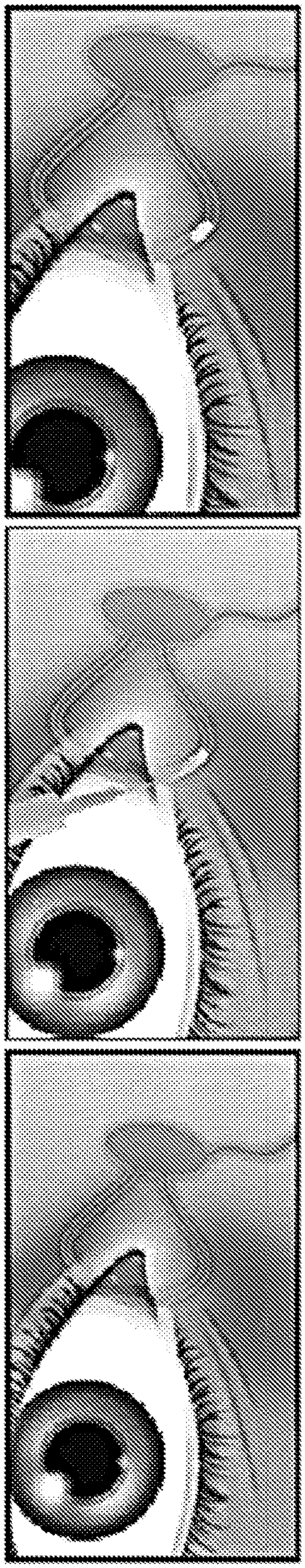
FIG. 12 illustrates one possible application of the devices, in accordance with various embodiments of the present disclosure. This example can include injecting a thermally responsive hydrogel into the tear duct, where it changes state from a fluid to a solid or semi-solid, thus occluding the pathway.
Figure 14:
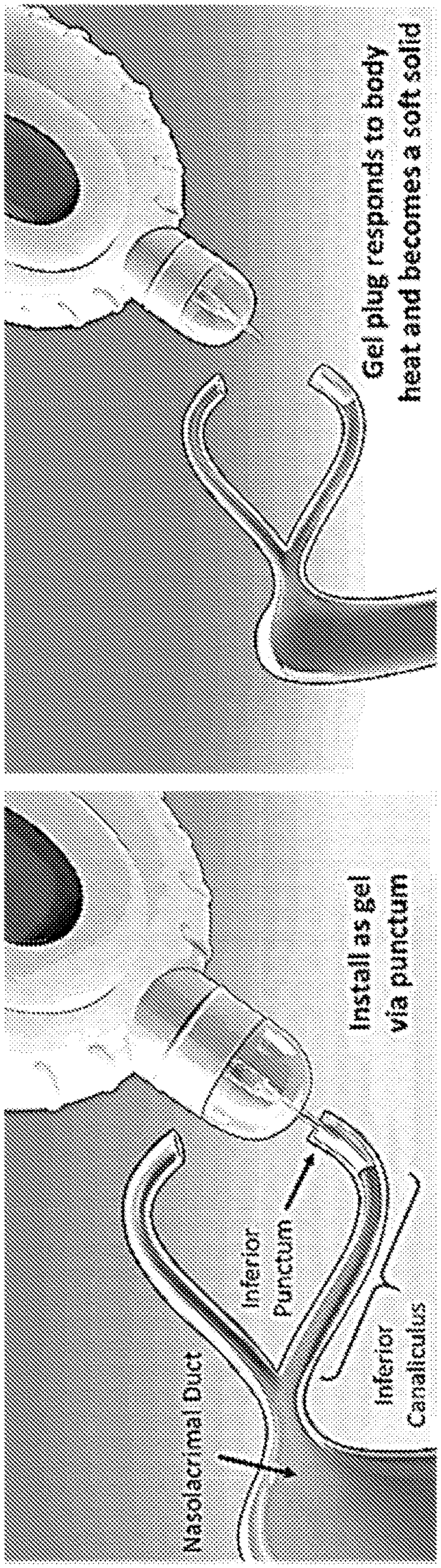
Figure 15:
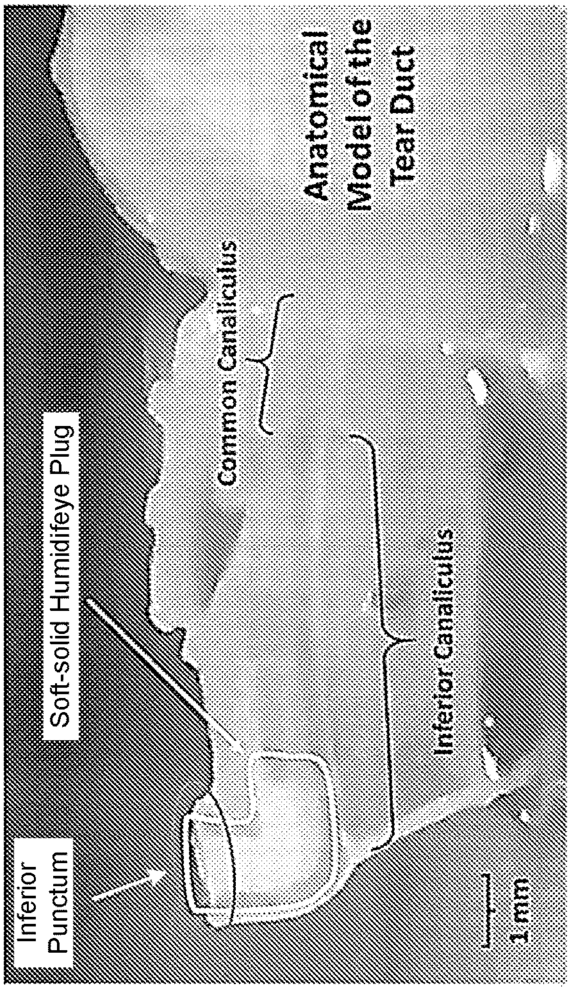
FIG. 15 is an image illustrating a punctal plug adapted to flexible silicone in a tear duct model, in accordance with various embodiments of the present disclosure.

This embodiment involves a novel technique for administration of a proprietary, thermally responsive hydrogel into the tear duct. FIG. 12 and FIG. 15 illustrate an example of the injection of the hydrogel in a tear duct. This example can include injecting the thermally responsive hydrogel into the tear duct, where it changes state from a fluid to a solid or semi-solid, thus occluding the pathway. The hydrogel can be a viscous fluid at the time of injection, adapting to the internal shape of the tear duct. The hydrogel can then solidify as it equilibrates to body temperature. By creating a form-fitting occlusion within the duct as shown in FIG. 12 and FIG. 14, a greater amount of moisture is retained on the eye's surface. Further, the sensation of having something stuck inside the duct is minimized. The table below describes the undesirable features of current treatments and how the current disclosure presents a better experience.

| Modality | Problems | Benefits of Disclosure |
|---|---|---|
| OTC Eye Drops | Requires continuous use.<br>May cause blurred vision over extended periods.<br>Difficult for patient to | One-time office visit<br>Visual side effects are very uncommon<br>Administered in minutes |

-continued

| Modality | Problems | Benefits of Disclosure |
|---|---|---|
| | administer accurately | by licensed physician |
| Pharmaceutical Eye Drops | Manifestation of therapeutic effects often require continuous use for extended periods. | One-time office visit for non-chemical solution that provides immediate results. |
| | Side effects may include: irritation, burning itching, decreased visual acuity. | Side effects are very uncommon. |
| | Difficult for patient to administer accurately. | Administered in minutes by licensed physician. |
| Pre-Molded Plugs | Sizing is not custom, and may cause patient discomfort | Plug is a shape adaptable, custom fit for every patient |
| | May abrade the sclera and cause discomfort with contact lenses | Plug is soft and rests below the surface of the punctum |
| | Very common for plugs to become dislodged within the first several months of use due to poor fit. | Accurate fit allows plug to remain in the tear duct more reliably |
| In-situ hydrating Plugs | Can cause difficulties when removal is desired | Smart material is reversible and easily removable |

The benefits of treatment by means of this disclosure are as follows: by providing a pre-filled, single-use device with a single, binary trigger for injection of a shape adaptable plug material, both doctors and patients will benefit from a streamlined procedure that minimizes discomfort and risk of complication. This disclosure offers a one-size-fits-all solution and precludes doctors from performing anatomical measurements and selection between different plug types and sizes.

The installation of alternate lacrimal occlusion plugs can primarily comprise the following: manual injection by syringe & needle, forceps, or an instrument which press-fits a mounted plug and then releases it by retracting the retaining element. Such devices require more skill, coordination, and have greater potential sources of error than the disclosed devices when presented for the same application.

Design Considerations for Dry Eye Application

Figure 13:
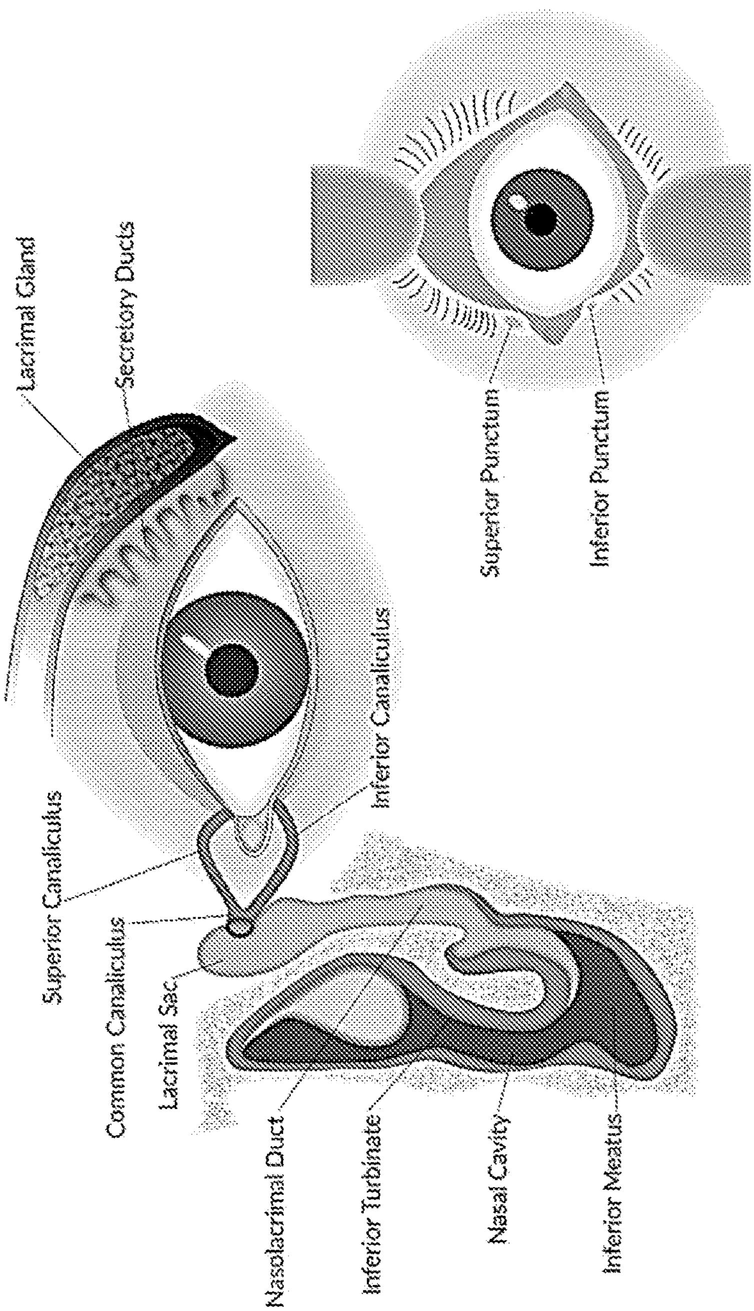
FIGS. 13 and 14 illustrate an example of nasolacrimal anatomy and use of a punctal plug injector, in accordance with various embodiments of the present disclosure.

FIGS. 13-15 show diagrams of nasolacrimal anatomy and an example of a possible use as a punctal plug injector. In some aspects the amount of fluid injected and the dynamics of injection would produce a lacrimal occlusion efficiency of about 40%-60%, in some other aspects an occlusion efficiency of about 60-80% may be desirable, in another aspect, an occlusion of about 80-100% may be desirable, and in yet another aspect, a full 100% occlusion may be desirable. It should be understood that occlusion efficiency may be the result of incomplete, or channel-imbued occlusion or of occlusive material porosity. Further, any permutation of numbers within and across the ranges described above may be considered a viable range for potentially desirable occlusion efficiency, relative to the individual needs of patients and healthcare practitioners.

In some aspects, the interface at the anatomical site of injection will not create a strong or complete seal around the punctum, thus allowing for fluid to exit the punctum around the dispensing cannula if a particular pressure threshold is met. In another aspect, a strong, complete seal may be implemented in order to ensure that that the cavity is filled to the maximum volume allowed by the compliance of the surrounding tissue and the depth of the fluid before transition to a solid. In some aspects, a feature for ensuring proper sealing may involve a pliable sheath that is constricted by the diameter of the punctum, but other feature to achieve this function are also considered outside of the above example.

In some aspects, the outer diameter of the injection port entering the punctum is small enough to comfortably enter without the need for dilation, as illustrated by FIG. 14. In such an aspect, the outer diameter may be smaller than the average punctal diameter or slightly larger, accounting for the compliance of the tissue. The injection port tube can be blunt-tipped and can be sized with an outer diameter of about 0.3 mm to about 1.1 mm. In some aspects, there is an injection port diameter or a joined component, such as one for creating a seal, that is notably larger than the average punctal diameter and which may require dilation may be desirable; in which event the diameter would be expected to lie within the range of about 0.6 mm and about 2.5 mm. Note that the above ranges pertain only to the application of applying a plug to the tear duct, and that these numbers do not represent or preclude other use cases for a similar device.

In some aspects, the injection port can be constructed such that it remains stiff and resistant to buckling, but elastic enough to bend and deflect from a range of about 0° to about 90°. In some aspects, but not all, this may involve a biocompatible material including, but not limited to polycarbonate, PEEK, polyimide, stainless steel (for example, as a smooth-edged hypotube), PEBAX, PTFE or other material featuring a stiffness of greater than about 0.5 GPa). In some aspects this may result in a ratio of exposed injection port length to wall thickness that is determined by the axial forces that can reasonably be expected in a given application. For a low force scenario this may result in a ratio of about 0.005 or higher. Note that the above ranges pertain only to the application of applying a plug to the tear duct, and that these numbers to not represent or preclude other use cases for a similar device.

In some aspects, a hypodermic needle, or similar construction may be involved for installing a substance in a different manner to provide benefits through an alternate mechanism. The injection device or cartridge can be configured to connect via standardized fluid management fitting to hypodermic needles, blunt tipped needles, tubing, catheters, etc. to enable modularity of delivery method and delivery site.

In some aspects, the inner diameter of the injection port entering the punctum can be as large as is feasible to allow for the desirable mechanical and structural properties; expected to fit within a range of about 0.2 mm to about 1.0 mm, depending on the support available and force applied to the injection port. In some other aspects, the inner diameter may be minimized as a means of controlling fluid flow as it leaves the injection port's cannula. Note that the above ranges pertain only to the application of applying a plug to the tear duct, and that these numbers to not represent or preclude other use cases for a similar device relevant to the disclosure. In some aspects, the inner diameter is small enough relative to the viscosity of the fluid that the surface tension inside the reservoir is sufficient to prevent excessive leakage through the cannula.

In some aspects, the preferred exposed length of the injection port for the application of a plug to the tear duct is such that it is easily visualized and allows easy access to the tear duct, without being so long as to enter the punctum and cause injection to occur exceedingly deep into the tear duct, to perforate the tissue of the tear duct, to cause a large enough gap between the device and the tear duct that control is negatively affected, or to create such a long fluid conveying channel that the appropriate volume is not dispensed, excessive fluid is retained, or is dispensed with undesirable qualities. An appropriate exposed tip length is expected to range from about 0.5 mm to about 10 mm, or from about 1 mm to about 5 mm, or about 2 mm to 4 mm. Note that the above ranges pertain only to the application of applying a plug to the tear duct, and that these numbers to not represent or preclude other use cases for a similar device relevant to the disclosure, such as, for example, the case of a hypodermic needle-style injection port, for which exposed length is expected to range from about 0.5 mm to about 100 mm, or about 5 mm to about 50 mm.

It is preferred that the dispensed volume is sufficiently large that the largest anticipated anatomical dimensions may be fully occluded (or with the intended range of occlusion efficiency) and remain secure while under pressure, but sufficiently small that the fluid does not overfill the smallest anticipated anatomy to the extent that fluid enters the lacrimal sac or that significant fluid is wasted by flow back out of the punctum. As described, it is desirable that the fluid flows deep enough to transition to a solid or semi solid while in contact with sufficient surface area as to hold securely under pressure, but not so deep as to infiltrate the nasolacrimal sac, as this may increase the risk for health concerns. Note that depth is affected by anatomical dimensions, tissue compliance, injection speed, back-pressure, and rapidity of phase transition. Thus, in some aspects, a larger volume than may be contained by the anatomy at-rest may often be dispensed without risk of entry into the nasolacrimal duct and resulting in backflow of material out of the punctum, which may be wiped away to provide a plug that is nearly flush with the entry point. Nevertheless, it may be considered beneficial to reduce the dispensed volume to the best extent possible, in order to reduce potential for complication and facilitate any potential need for removal. The range of dispensed volume expected to achieve maximum safe depth relative to anatomical variability in the majority of adults is about 1 μL to about 15 μL, or about 1.5 μL to about 8 μL or about 2 μL to about 5 μL. The range of practical initial fluid volumes is expected to lie between about 1 μL to about 100 μL, depending on the injection efficiency. In this case, a conservative injection efficiency of 50% is given as example, however this should not be construed as precluding the possibility of different volumes with respect to different injection efficiencies. Further, the above remains accurate in the case of a design configured to present a fully primed system where the reservoir is overfilled and retains fluid after injection due to geometric constraints on the stoppers advancement, as illustrated by examples in FIGS. 11C and 11D.

In some aspects, the actuation mechanism and reservoir can be configured to deliver a volume of about 1 μL to about 20 μL or about 2 μL to about 5 μL to a tear duct in about 5 seconds or less.

In some aspects, the injection volume may be considered arbitrary. For example, when applying the hydrogel to a tear duct, which is sealed by the injection device, it may be possible that the resulting injection volume is self-regulating, depending on the internal volume of the tear duct and the resulting back-pressure. In some aspects, a smaller channel may produce a greater internal pressure, thereby counter-acting the pressure dispensing the fluid and reducing the total amount of fluid administered, compared to a larger channel. However, due to a difference in hydrogel contact surface area, it may be that the smaller channel needs less volume to be filled than the larger channel in order to be effective. In this case, it may be that a similarly desirable result is achieved in both cases, regardless of the selected injection volume.

In some aspects, the injection port is secured to a hub component which serves as a junction for the fluid reservoir, forming a connection between the reservoir and the injection port, as illustrated by FIGS. 11C and 11D. In some aspects of this component, the distal surface is domed and smooth so that it may serve as a convenient and atraumatic interface when making contact with the patient. In some aspects, the exposed tip length may be short enough that the hub can rest comfortably on the eyelid without pressing hard into the tissue within the punctum; with such a length described above, with an example of length relative to tear duct dimensions illustrated in FIG. 14. In some aspects, this hub may be connected to a structural body component, by snap fit, threading, or other feature. In some aspects this may be a component that is replaceable, serving as a refill for injection, and may include a stopper, which is decoupled from an effecting plunger component. In some aspects, where the hub and reservoir are in contact with a stopper, the contacting materials can be optimized for minimal friction, by using a low degree of diametric interference of about 0.1% to about 10%, or about 2% to about 8%, by using a material with a low coefficient of friction of about 1.0 or lower, or about 0.75 or lower, or about 0.5 or lower, or by reducing the contacting surface area of the two components (e.g., through the use of ridges, as illustrated by examples in FIGS. 11E and 11F), as some examples, and optimized for minimal moisture permeability, by using the materials and techniques described above and/or using a thickness proportional to the desired transmission rate. In some aspects, this component is transparent, so as to enable visualization of the fluid inside, which in some aspects, may reflect information relevant to injection efficacy. An example for this visualization is the case where a thermally responsive hydrogel becomes opaque and coloured when undergoing a change in properties, for example, to a more solid state, which would be make it resistant to injection until such a time as it has cooled enough to return to a fluid state.

In some aspects it may be useful for one device to contain the dosage necessary for the treatment of two eyes.

All mechanical modalities and considerations described above should be considered to have been conceived of in all possible combinations and permutations and are also conceived of in the context of the following application areas.

Other Applications

The injection devices can be utilized in a wide range of applications such as, but not limited to:

- Administration of multiphase materials.
- Storage and/or administration of environmentally sensitive, low-volume materials
- For use in electronics insulating, adhering, or catalyzing elements in a specific area, channel, or footprint.
- For cosmetic or recreational applications, application of dye or drug or nutraceutical substances.
- For delivering medicament to the nasal passageways for relieving of congestive symptoms or other ailment (e.g., through nasolacrimal system or through nasal passage).
- For delivering a solid cylinder, such as a needle or a plug.
- Delivery of liquid, gel, aerosol, suspension, powder.
- Delivery of materials intended to remain for a period of time.
- Delivery of materials intended to be removed, via flushing, ambient dissipation, or otherwise.
- Delivery of medicament or hydrogel-compounded or therapeutic drug-releasing product.
- Delivery of materials (e.g., imaging contrast, diagnostic aid, drug release, etc.) intended to pass all the way through the subject performing some function in-route.

Delivery of pharmaceutical, biological, or otherwise therapeutic compounds subcutaneously or to some specific internal anatomy The injection device can comprise mechanisms, components, assemblies, and/or features enabling safe and effective delivery of a shape adaptable material to the tear ducts, substance property-protecting material and design considerations, mechanical features enabling controlled delivery of viscous and/or non-Newtonian fluids, formulations, and responsive materials, mechanical features enabling automatic, velocity-scaled injection, and/or mechanical features enabling precise, rapid delivery of very small volumes about and including 1 mL or less. Velocity can be controlled and scaled down by selection of spring parameters, such as constant (k), deflection, allowed firing distance; or in the case of a torsion spring, the radial equivalents, as well as the thread pitch of a worm gear or gear ratio configurations. The pre-injection material (in the reservoir) can be insulated against external factors and/or can actively have external factors countered which may otherwise affect the fluids desirable properties for a given application. The injection device can comprise multiple reservoirs permitting multiple injections, from one location on the device or more. The dosage may be adjusted or delivered in defined steps, up to a maximum dosage. In some aspects, these modular doses may reflect the level of occlusion in range from about 40% to about 100%. A combination of the reservoir and stopper may be optimized for prevention of trapped air. An injection system can comprise a primary reusable device component and prefilled, refill/cartridge components for injection. The injection device can be configured as a prefilled unit or aggregate of units, including prefilled cartridges, to store and deliver volumes of, e.g., about 0.01 μL to about 10 mL or about 0.1 μL to about 1 mL, or about 1 μL to about 100 μL.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed:

1. An injection device, comprising:

an injection port configured to deliver a shape adaptable material, the injection port comprising a straight, blunt-tipped tube extending between an inlet at a proximal end and an outlet at a distal end, the injection port having a substantially constant diameter along its length and a fixed exposed length of about 1 mm to about 5 mm;

a junction component coupled to a body of the injection device and to the proximal end of the injection port, the junction component comprising a sealed reservoir configured to contain and store the shape adaptable material for ejection through the injection port, the reservoir having a diameter in a range from about 0.1 mm to less than 5 mm and a ratio of the diameter to a primed length from about 1:1000 to about 10:1 the junction component further comprising a linear dispensing channel having a length extending between a first end at a distal end of a barrel of the reservoir and a second end at the inlet of the injection port, the linear dispensing channel comprising an intermediate chamber adjacent to the distal end of the barrel, the intermediate chamber having a barrel diameter in a range of about 25% to about 95% of a barrel diameter of the reservoir; and an actuation mechanism comprising a stopper that engages with and seals the reservoir, where activation of the actuation mechanism forces the stopper into the reservoir thereby controlling ejection of the shape adaptable material through the injection port, where the actuation mechanism ejects a defined injection volume of the shape adaptable material at a rate of less than 50 μL/second in a range from about 0.1 μL to about 20 μL of the shape adaptable material having a viscosity greater than 3000 cp, the actuation mechanism ejecting the defined injection volume of the shape adaptable material from the reservoir through the injection port by advancing the stopper a predefined length into the reservoir.

2. The injection device of claim 1, wherein the actuation mechanism comprises a spring that forces the stopper into the reservoir via a plunger.

3. The injection device of claim 2, wherein the spring is a compression spring sized to provide an axial force based upon properties of the shape adaptable material being ejected.

4. The injection device of claim 3, wherein the spring is extended when the actuation mechanism is activated.

5. The injection device of claim 4, wherein the spring is compressed to a fully loaded length in a range from about 10% to about 50% of a free length of the spring before activation.

6. The injection device of claim 4, wherein active extension of the spring or translation of the plunger during activation contacts the stopper and imparts a force to a rear portion of the stopper axially compressing and radially expanding the stopper thereby increasing an interference fit with an inner surface of the reservoir as the stopper advances over the predefined length.

7. The injection device of claim 6, wherein the stopper is coupled to the plunger via a prong extending an axial length from a distal end of the plunger and a complementary stopper cavity, wherein the axial length of the prong is less than an axial length of the complementary stopper cavity, where the axial length is along a lengthwise axis of the plunger.

8. The injection device of claim 4, wherein active extension of the spring or translation of the plunger during activation contacts a distal surface of an internal cavity of the stopper and imparts a force along a central axis of the stopper that radially contracts the stopper thereby reducing an interference fit with an inner surface of the reservoir.

9. The injection device of claim 4, wherein the spring provides an injection force at about 30% compression or less of a free length of the spring that exceeds a break-loose resistance force experienced by the stopper to initiate and then maintain translation within the reservoir after activation.

10. The injection device of claim 9, wherein a rate of injection is based upon an amount of compression of the spring, the rate of injection in a range from about 0.2 μL/second to less than 50 μL/second.

11. The injection device of claim 2, wherein the stopper is coupled to an end of the plunger.

12. The injection device of claim 11, wherein force transmission between the stopper and the plunger causes radial contraction of the stopper after activation.

13. The injection device of claim 11, wherein force transmission between the stopper and the plunger causes radial expansion of the stopper after activation.

14. The injection device of claim 11, wherein the stopper is coupled to the plunger via a prong and a complementary cavity of the stopper.

15. The injection device of claim 14, wherein a length of the prong is greater than a length of the complementary cavity, wherein the prong is not mated by a thread, and a distal end of the prong initiates the plunger's transmission of a force to a distal end of the complementary cavity.

16. The injection device of claim 15, wherein extension of the prong into the complementary cavity radially contracts the stopper thereby decreasing an interference fit with an inner surface of the reservoir.

17. The injection device of claim 16, wherein a face of the plunger contacts the stopper from the proximal end after a distal end of the stopper makes contact with a distal end of the reservoir, thus axially compressing and radially expanding the stopper thereby increasing an interference fit with an inner surface of the reservoir.

18. The injection device of claim 2, wherein the stopper and the plunger are a single part.

19. The injection device of claim 1, wherein the predefined length is in a range from about 0.25 mm to about 10 mm.

20. The injection device of claim 1, wherein advancement of the stopper into the reservoir is limited to a predefined length away from a distal end of the reservoir until the injection device is activated.

21. The injection device of claim 20, wherein the reservoir has an axial length (L) between a proximal end and the distal end of the reservoir and the predefined length is about 9/10 of the axial length (0.9 L) or less from the distal end of the reservoir.

22. The injection device of claim 1, wherein the stopper comprises material having a shore hardness in a range from OA to about 90A.

23. The injection device of claim 22, wherein the shore hardness is in a range from about 55A to about 75A, and an interference of the stopper with an inner surface of the reservoir is about 2% to about 20%.

24. The injection device of claim 1, wherein the stopper comprises material having a tensile modulus at 100% strain in a range from about 0.1 MPa to about 10 MPa, wherein the material does not comprise silicone.

25. The injection device of claim 24, wherein the tensile modulus is in a range from about 1 MPa to about 3 MPa.

26. The injection device of claim 1, wherein the actuation mechanism uses pneumatic force to move a plunger or act directly on the stopper to move it through the reservoir.

27. The injection device of claim 26, wherein the stopper maintains an effective dynamic seal by radially expanding in response to the pneumatic force applied to the stopper.

28. The injection device of claim 26, wherein the actuation mechanism relies on a user to compress a fluid manually or releases a pre-compressed fluid to apply the pneumatic force to the plunger or stopper.

29. The injection device of claim 1, wherein the actuation mechanism comprises one or more elements which are manually manipulated to apply pressure to force the stopper into the reservoir.

30. The injection device of claim 1, wherein the actuation mechanism comprises gears that translate rotation to axial movement of the stopper in the reservoir.

31. The injection device of claim 1, wherein the actuation mechanism comprises one or more elements which are deformed, pressed, rotated, or translated inwardly to transmit force non-axially to cause expansion or movement in the axial direction to force the stopper into the reservoir.

32. The injection device of claim 1, wherein the shape adaptable material comprises a non-Newtonian material.

33. The injection device of claim 1, wherein the viscosity of the shape adaptable material is less than 20,000 cp.

34. The injection device of claim 1, wherein the shape adaptable material is a non-Newtonian, multiphase hydrogel compounded for elution of a drug, biological, or therapeutic substance.

35. The injection device of claim 1, wherein a volume of the shape adaptable material present in the reservoir is about 110% to about 1000% of a total injectable volume delivered by the injection device.

36. The injection device of claim 35, wherein the shape adaptable material present in the reservoir is retained in both the injection port and a portion of the reservoir proximal to the injection port after the stopper has traveled to the end of the reservoir, ejecting the defined injection volume.

37. The injection device of claim 1, wherein the reservoir geometry enables purging of air from a filled reservoir through or by the stopper during introduction of the stopper into the reservoir.

38. The injection device of claim 1, wherein the reservoir has a geometry that facilitates laminar fluid flow of the shape adaptable material through the injection port as the stopper is forced into the reservoir.

39. The injection device of claim 38, wherein adjacent sections of the linear dispensing channel use structural curvatures to smoothly transition into intermediate sections of varying diameters between the distal end of the barrel and the inlet of the injection port.

40. The injection device of claim 39, wherein the varying diameter of each intermediate section is smaller than the diameter of the reservoir, but larger than an inner diameter of a dispensing cannula, and decreases between the distal end of the barrel of the reservoir and the inlet of the injection port.

41. The injection device of claim 1, wherein a transition between the barrel and the intermediate chamber has a curvature of radius of about 20% to about 100% of the barrel diameter of the intermediate chamber.

42. The injection device of claim 1, wherein the reservoir and seals made by the stopper and an injection port cover mitigate fluid or gas transmission into or from the reservoir and injection port.

43. The injection device of claim 42, wherein the junction component, stopper, and injection port cover are fabricated with low permeability materials with a water diffusion coefficient of about $1\times10^{-6}$ $cm^2/s$ or less or a moisture vapor transmission rate of about 10 $g/m^2/day$ or less.

44. The injection device of claim 42, wherein the junction component comprises glass, metal, cyclic olefin polymers or copolymers, or cyclic olefin or metal compounded or layered materials.

45. The injection device of claim 42, wherein the stopper comprises fluorocarbon, fluoroelastomer, TPE or TPV.

46. The injection device of claim 1, wherein the injection port tube is configured to deliver the shape adaptable material into a tear duct, which sustains its adapted shape in the tear duct.

47. The injection device of claim 46, wherein the shape adaptable material forms an occlusive plug in the tear duct.

48. The injection device of claim 47, wherein the shape adaptable material changes properties from a flowable liquid to a more viscous liquid, semi-solid or solid.

49. The injection device of claim 46, wherein the injection port tube has an outer diameter in a range from about 0.3 mm to about 0.6 mm.

50. The injection device of claim 49, wherein the injection port tube has a ratio of wall thickness to length of about 0.005 or greater.

51. The injection device of claim 1, wherein the injection port tube comprises polycarbonate, PEEK, polyimide, PEBAX, or stainless steel.

52. The injection device of claim 1, wherein the shape adaptable material is a polymer hydrogel.

53. The injection device of claim 52, wherein the polymer hydrogel comprises a NIPAM (N-lsopropylacrylamide) monomer.

54. The injection device of claim 53, wherein the polymer hydrogel comprises one or more additional monomers.

55. The injection device of claim 52, wherein the polymer hydrogel comprises a cross-linking monomer or excipient.

56. The injection device of claim 1, wherein the injection port has a ratio of wall thickness to length of about 0.005 or greater.

57. The injection device of claim 1, wherein the injection port has a ratio of inner diameter to length in a range from about 1:1000 to about 4:1.

58. The injection device of 1, wherein the reservoir comprises a cartridge configured to contain a predefined volume of the shape adaptable material.

59. The injection device of claim 58, wherein the junction component is a disposable component with the reservoir prefilled with the predefined volume of the shape adaptable material.

60. The injection device of claim 59, wherein the body and the actuation mechanism are reusable as an independent subassembly from the junction component and the reservoir.

61. The injection device of claim 1, wherein the injection device is a disposable device with a single reservoir prefilled with a predefined volume of the shape adaptable material and provided ready-to-use at a point-of-care, wherein the stopper cannot travel any further after a first or second activation of the injection device.

62. The injection device of claim 1, comprising an activation trigger configured for a digit of a user to activate the actuation mechanism.

63. The injection device of claim 62, wherein the activation trigger comprises a button configured to engage with the plunger.

64. The injection device of claim 63, wherein the digit-activated button arrests the plunger and stopper combination at a position in the reservoir where the position determines the defined injection volume of the shape adaptable material for injection upon activation.

65. The injection device of claim 62, wherein the activation trigger comprises a lever configured to activate the actuation mechanism.

66. The injection device of claim 1, wherein the body encases the actuation mechanism, the body sized to fit in a user's hand.

67. The injection device of claim 1, comprising a cartridge connected to the reservoir or acting as the reservoir containing the shape adaptable material, the cartridge replaceable by an equivalent cartridge after each use.

68. The injection device of claim 67, wherein the cartridge is the junction component comprising a seal at both ends.

69. The injection device of claim 1, wherein the junction component is integrated in the body.

70. The injection device of claim 1, wherein the junction component comprises polycarbonate, polypropylene, polyvinyl chloride, PET, PETG, cyclic olefin polymers or copolymers, or cyclic olefin or metal compounded or layered materials, or metal.

71. The injection device of claim 1, wherein the stopper and an injection port cover comprise fluorocarbon, fluoroelastomer, silicone, urethanes, TPE, or TPV.

72. The injection device of claim 1, wherein the reservoir is prefilled with a predefined volume of the shape adaptable material in a range from about 0.01 μL to about 1 mL.

73. The injection device of claim 72, wherein at least 90% of the predefined volume is delivered to a target location within a predefined time of activation of the injection device without use of a sensor.

74. The injection device of claim 73, wherein the predefined time is about 5 seconds or less.

75. The injection device of claim 72, wherein the predefined volume of shape adaptable material contained within the reservoir is greater than the defined injection volume, wherein a remainder of the shape adaptable material is retained in both the injection port and a portion of the reservoir proximal to the injection port after the stopper has traveled to the end of the reservoir.

76. The injection device of claim 1, wherein the predefined volume contained by the reservoir is about 5% to about 2000% more than a total injectable volume deliverable from the reservoir, regardless of a quantity of discrete injections enabled by the injection device.

77. The injection device of claim 1, wherein the shape adaptable material comprises a polymer hydrogel comprising a concentration of 0.2% to 70% polymer or copolymer.

78. The injection device of claim 1, wherein the shape adaptable material has a viscosity of 5000 cp or greater.

79. The injection device of claim 1, wherein the injection device is configured to provide an indication of integrity or readiness of the shape adaptable material or the injection device, independent of dose.

80. The injection device of claim 79, wherein the junction component is optically translucent or transparent providing visual access to the shape adaptable material contained in the reservoir.

81. The injection device of claim 1, wherein the injection device comprises radiation compatible materials suitable for radiation exposure above background radiation levels up to a cumulative radiation dose, where the cumulative radiation dose acquired by the radiation compatible materials during exposure to radiation is about 100 kGy or less.

82. The injection device of claim 1, wherein the junction component comprises an activatable heating or cooling element for conditioning of the shape adaptable material before injection.

83. The injection device of claim 1, wherein the reservoir comprises a barrier configured for removal allowing a combination of substances separated by the barrier to be mixed prior to injection.

84. The injection device of claim 83, wherein the mixing of the substances at time of use forms the shape adaptable material.

85. The injection device of claim 1, wherein the exposed length of the injection port is about 2 mm to about 4 mm.

86. The injection device of claim 1, wherein the actuation mechanism ejects about 16 μL or less of the shape adaptable material.

* * * * *